United States Patent [19]

Fake et al.

[11] Patent Number: 4,590,192
[45] Date of Patent: May 20, 1986

[54] BENZISOTHIAZOLES, THEIR PHARMACEUTICAL COMPOSITIONS, AND METHOD OF USE

[75] Inventors: Charles S. Fake; Gordon Burrell, both of Harlow, England

[73] Assignee: Beecham Group p.l.c., Brentford, England

[21] Appl. No.: 537,048

[22] Filed: Sep. 29, 1983

[30] Foreign Application Priority Data

Oct. 1, 1982 [GB] United Kingdom ............... 8228150
Jul. 28, 1983 [GB] United Kingdom ............... 8320326

[51] Int. Cl.$^4$ ..................... A61K 31/38; C07D 417/12
[52] U.S. Cl. .................................. 514/231; 548/181; 548/198; 548/212; 548/134; 548/136; 544/133; 544/134; 544/135; 546/198; 514/321; 514/373
[58] Field of Search ............... 548/212, 181, 136, 134; 546/198; 424/267, 270; 544/133, 134, 135

[56] References Cited

U.S. PATENT DOCUMENTS

| | | | |
|---|---|---|---|
| 3,905,984 | 9/1976 | Durant et al. | 548/329 |
| 4,022,797 | 5/1977 | Durant et al. | 548/329 |
| 4,053,473 | 10/1977 | Durant et al. | 548/329 |
| 4,104,387 | 8/1978 | Wade et al. | 544/368 |
| 4,128,658 | 12/1978 | Price et al. | 546/201 |
| 4,147,698 | 4/1979 | Wade et al. | 548/212 |
| 4,165,378 | 8/1979 | Gilman et al. | 548/337 |
| 4,220,654 | 9/1980 | Bolhofer et al. | 548/342 |
| 4,490,527 | 12/1984 | Schiehser et al. | 544/62 |

FOREIGN PATENT DOCUMENTS

| | | | |
|---|---|---|---|
| 67436 | 12/1982 | European Pat. Off. | 548/212 |
| 81955 | 6/1983 | European Pat. Off. | 544/62 |
| 590963 | 2/1959 | Japan | 544/321 |
| 656470 | 3/1965 | Japan | 546/87 |
| 506422 | 11/1981 | Spain | 549/495 |
| 2075980A | 11/1981 | United Kingdom | 549/495 |

OTHER PUBLICATIONS

M. E. Parsons, Ph.D. thesis, University of London (1969).
E. W. Gill and H. R. Ing, "Furan and Tetrahydrofuran Compounds Analogous to Ganglionblocking Agents of the 3-Oxapentane-1:5-bistrialkylammonium Series", *J. Chem. Soc.*, 1958, pp. 4728–4731.
M. N. Ghosh and H. O. Schild, "Continuous Recording of Acid Gastric Secretion in the Rat", *Brit. J. Pharmacol.*, 13, pp. 54–61 (1958).
G. H. Hamor, "Saccharin Derivatives II; Synthesis of 4-Nitro-saccharin and Related Compounds", *J. Amer. Pharm. Soc.*, 49, 280 (1960).
Parke and Williams, "J. Chem. Soc.", (1950), pp. 1760–1763.

*Primary Examiner*—Robert T. Bond
*Attorney, Agent, or Firm*—James F. Haley, Jr.; Paul H. Ginsburg; David K. Barr

[57] ABSTRACT

Compounds of formula (I), or a pharmaceutically acceptable salt, quaternized derivative, N-oxide or solvate thereof:

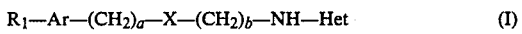

$$R_1-Ar-(CH_2)_a-X-(CH_2)_b-NH-Het \quad (I)$$

wherein: the substituents are defined in the specification.

The compounds are useful in treating excess gastric acid secretions such as peptic ulcers.

18 Claims, No Drawings

BENZISOTHIAZOLES, THEIR PHARMACEUTICAL COMPOSITIONS, AND METHOD OF USE

The present invention relates to novel compounds having pharmacological activity, to processes and intermediates for their preparation, to pharmaceutical compositions containing them, and to their use in the treatment of mammals.

U.S. Pat. No. 4,128,658 discloses a class of aminoalkylfuran derivatives that are histamine H$_2$-receptor antagonists and that, therefore, are useful in the treatment of disorders relating to excess gastric acid secretion. One such derivative is the compound, N-[2-[[[5-(dimethylamino)methyl-2-furanyl]methyl]thio]ethyl]-N'-methyl-2-nitro-1,1-ethenediamine, which is commonly known as ranitidine.

A structurally distinct class of compounds has now been discovered. In addition, such compounds have been found to be histamine H$_2$-receptor antagonists. They are, therefore, useful in the treatment of disorders relating to excess gastric acid secretion, such as peptic ulcer and Zollinger-Ellison syndrome.

Accordingly, the present invention provides a compound of formula (I), or a pharmaceutically acceptable salt, quaternised derivative, N-oxide or solvate thereof:

$$R_1-Ar-(CH_2)_a-X-(CH_2)_b-NH-Het \quad (I)$$

wherein: R$_1$ is hydrogen, halogen, hydroxy, C$_{1-4}$ alkyl, C$_{1-4}$ alkoxy, or amino or guanidino, the or any amino moiety being optionally substituted by one or two C$_{1-4}$ alkyl optionally substituted by halogen, or an aminomethylene group of formula (a),

in which R$_2$ and R$_3$ are the same or different and are hydrogen, C$_{1-4}$ alkyl, C$_{3-6}$ cycloalkyl, C$_{3-6}$ cycloalkyl-C$_{1-4}$ alkyl or phenyl C$_{1-4}$ alkyl, or R$_2$ and R$_3$ together with the nitrogen atom to which they are attached are morpholino, pyrrolidino or piperidino;

Ar is furandiyl, thiophendiyl, phenylene, pyridinediyl, pyrimidinediyl, thiazolediyl, thiadiazolediyl or imidazolediyl;

a is 0 or an integer 1 or 2;

X is —S—, —O—, —CH$_2$—,

or —NH—;

b is an integer from 2 to 5; and

Het is a bicyclic heteroaryl group of formula,

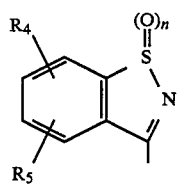

in which R$_4$ and R$_5$ are the same or different and are hydrogen, halogen, C$_{1-6}$ alkyl, trifluoromethyl, nitro, cyano, hydroxy, C$_{1-6}$ alkoxy, C$_{1-6}$ alkylthio, carboxy, amino, aminocarbonyl, aminocarbonylamino, amino-thiocarbonylamino, aminosulphonyl, C$_{1-6}$ alkylsulphonyl, C$_{1-6}$ alkylsulphinyl, C$_{1-6}$ alkylsulphonylamino, C$_{1-6}$ alkylsulphinylamino, phenylsulphonyl, phenylsulphinyl or are a group of formula (d) or (e), $$R_6-CY- \quad (d)$$

$$R_6-CY-Z- \quad (e)$$

in which R$_6$ is hydrogen, C$_{1-6}$ alkyl, C$_{1-6}$ alkoxy, C$_{1-6}$ alkylthio, phenyl, phenoxy or phenylthio, Y is oxygen or sulphur and Z is oxygen, sulphur or N—R$_7$, R$_7$ being hydrogen or C$_{1-6}$ alkyl, the C$_{1-6}$ alkyl group or the C$_{1-6}$ alkyl moiety of any of the foregoing C$_{1-6}$ alkyl-containing groups for R$_4$ and R$_5$ being optionally substituted by phenyl, the amino group or the amino moiety of any of the foregoing amino-containing groups for R$_4$ and R$_5$ being optionally substituted by one or two C$_{1-6}$ alkyl, phenyl or phenyl-C$_{1-4}$ alkyl or optionally N-disubstituted by C$_{4-5}$ polymethylene, and the phenyl moiety of any of the foregoing phenyl-containing groups for R$_4$ and R$_5$ being optionally substituted by C$_{1-6}$ alkyl, C$_{1-6}$ alkoxy, halogen, nitro or trifluoromethyl, and n is 0 or an integer 1 or 2.

Examples of Ar include 2,5-furandiyl; 2,5-thiophendiyl; 1,3- and 1,4-phenylene; 2,3- and 2,4-pyridinediyl; 2,4-pyrimidinediyl; 2,4-thiazolediyl; 3,5-(1,2,4,)-thiadiazolediyl; and 2,4- and 4,5-imidazolediyl. Preferred examples of Ar include 2,5-furandiyl; 2,5-thiophendiyl; 1,3-phenylene; and 2,4-thiazolediyl. The most preferred example of Ar is 2,5-furandiyl.

When Ar is furandiyl, thiophendiyl or phenylene, R$_1$ is, preferably, an aminomethylene group of formula (a), as hereinbefore defined. In particular, R$_1$ is an aminomethylene group of formula (a), in which R$_2$ and R$_3$ are the same or different and are hydrogen, methyl, ethyl, cyclopropyl or cyclohexyl, or R$_2$ and R$_3$ together with the nitrogen atom to which they are attached are pyrrolidino or piperidino. Most preferably, R$_1$ is dimethylaminomethyl, pyrrolidinomethyl or piperidinomethyl.

When Ar is pyridinediyl, pyrimidinediyl, thiazolediyl, thiadiazolediyl or imidazolediyl, in particular thiazolediyl, R$_1$ is, preferably, hydrogen, halogen, hydroxy, C$_{1-4}$ alkyl, C$_{1-4}$ alkoxy, or amino or guanidino, the or any amino moiety being optionally substituted by one or two C$_{1-4}$ alkyl optionally substituted by halogen, or an aminomethylene group of formula (a), as defined hereinbefore. In particular, R$_1$ is hydrogen, halogen, such as bromo, C$_{1-4}$ alkyl, such as methyl, or guanidino, any amino moiety being optionally substituted by one or two C$_{1-4}$ alkyl.

Preferred examples of a are 0 and the integer 1. In relation to the preferred examples of Ar, a is, preferably, the integer 1 when Ar is 2,5-furandiyl, 2,5-thiophendiyl or 2,4-thiazolediyl and is, preferably, 0 when Ar is 1,3-phenylene.

Preferred examples of X include —S—, —O— and —CH$_2$—, in particular —S— and —O—.

Preferred examples of b are the integers 2, 3 and 4, especially the integers 2 and 3. In relation to the preferred examples of Ar, b is, preferably, the integer 2 when Ar is 2,5-furandiyl, 2,5-thiophendiyl or 2,4-thiazolediyl, and is, preferably, the integer 3 when Ar is 1,3-phenylene.

A sub-class of $R_4$ and $R_5$ is that wherein $R_4$ and $R_5$ are the same or different and are hydrogen, trifluoromethyl, nitro, cyano, hydroxy, $C_{1-6}$ alkoxy, $C_{1-6}$ alkylthio, or amino optionally substituted by one or two $C_{1-6}$ alkyl or phenyl $C_{1-4}$ alkyl or optionally N-disubstituted by $C_{4-5}$ polymethylene, or $C_{1-6}$ alkylsulphonyl or phenylsulphonyl, the phenyl moiety being optionally substituted by $C_{1-6}$ alkyl, $C_{1-6}$ alkoxy, halogen, nitro or trifluoromethyl, or are a group of formula (d) in which Y is oxygen and $R_6$ is as defined hereinbefore, or are a group of formula (e) in which Y is oxygen, Z is N—$R_7$ and $R_6$ and $R_7$ are as defined hereinbefore.

A further sub-class of $R_4$ and $R_5$ is that wherein $R_4$ and $R_5$ are the same or different and are hydrogen, halogen, $C_{1-6}$ alkyl, trifluoromethyl, nitro, cyano, $C_{1-6}$ alkoxy, or amino, aminocarbonylamino or aminosulphonyl, the amino moiety being optionally substituted by one or two $C_{1-6}$ alkyl, phenyl or phenyl-$C_{1-4}$ alkyl or optionally N-disubstituted by $C_{4-5}$ polymethylene, or $C_{1-6}$ alkylsulphonylamino or a group of formula (e) in which $R_6$ is hydrogen or $C_{1-6}$ alkyl, Y is oxygen and Z is NH.

Particular examples of $R_4$ and $R_5$, which may be the same or different, include hydrogen, chloro, bromo, iodo, methyl, trifluoromethyl, nitro, cyano, methoxy, amino, methylaminocarbonylamino, aminosulphonyl and formamido.

Preferred examples of $R_4$ and $R_5$, which may be the same or different, include hydrogen, nitro, amino, methylaminosulphonyl, dimethylaminosulphonyl, acetamido and propionamido. In particular, one of $R_4$ and $R_5$ is hydrogen and the other is hydrogen, nitro, amino, methylaminosulphonyl, dimethylaminosulphonyl, acetamido and propionamido. The preferred position for substitution by the other of $R_4$ and $R_5$ is the 4- or 6-position, especially the 4-position.

Preferably, n is an integer 1 or 2, in particular 2.

The compounds of the present invention are capable of existing as tautomers. The present invention extends to all such tautomers individually and as mixtures.

A pharmaceutically acceptable salt of a compound of the present invention is, preferably, a pharmaceutically acceptable acid addition salt. Examples of such a salt include an inorganic acid addition salt, such as a sulphate, nitrate, phosphate, borate, hydrochloride and hydrobromide, and an organic acid addition salt, such as an acetate, fumarate, tartrate, citrate, succinate, benzoate, ascorbate, methylsulphonate, α-ketoglutarate, α-glycerophosphate and glucose-1-phosphate. The hydrochloride salt is the most preferred pharmaceutically acceptable salt.

A quaternised derivative of a compound of the present invention includes a compound of the present invention quaternised by an optionally substituted alkyl halide, for example a $C_{1-4}$ alkyl, $C_{3-6}$ cycloalkyl, $C_{3-6}$ cycloalkyl $C_{1-4}$ alkyl or phenyl $C_{1-4}$ alkyl halide, such as a chloride, bromide or iodide.

The compounds of the present invention and their pharmaceutically acceptable salts form solvates with pharmaceutically acceptable solvents, for example hydrates.

Of the compounds exemplified hereinafter those that are preferred are the compounds of Examples 2, 18, 20, 21c, 21f, 21h, 21i and 25.

The present invention also provides a process for preparing a compound of formula (I), or a pharmaceutically acceptable salt, quaternised derivative, N-oxide or solvate thereof, which comprises reacting a compound of formula (II), or an acid addition salt thereof:

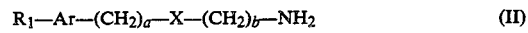

$$R_1—Ar—(CH_2)_a—X—(CH_2)_b—NH_2 \quad \text{(II)}$$

wherein $R_1$, Ar, a, X and b are as defined hereinbefore, with a compound of formula (III):

$$Het—L_1 \quad \text{(III)}$$

wherein Het is as defined hereinbefore and $L_1$ is a leaving group; in the case where n in the resulting compound of formula (I) is O, optionally oxidising the compound to obtain another compound of formula (I) wherein n is an integer 1 or 2; optionally converting $R_1$, $R_4$ or $R_5$ in the resulting compound of formula (I) into another $R_1$, $R_4$ or $R_5$; and optionally forming a pharmaceutically acceptable salt, quaternised derivative, N-oxide or solvate thereof.

The leaving group ($L_1$) is such as to be displaceable by the compound of formula (II). Examples of the leaving group ($L_1$) include halogen, such as chloro and bromo, $C_{1-4}$ alkoxy, such as methoxy and ethoxy, $C_{1-4}$ alkylthio, such as methylthio and ethylthio, $C_{1-4}$ alkylsulphinyl, such as methylsulphinyl, and thiol. Preferred examples of the leaving group ($L_1$) include chloro, methoxy, ethoxy, methylthio and thiol. Particularly preferred examples are chloro and ethoxy.

The reaction may be carried out in a solvent, such as dichloromethane, toluene, 2-methoxy-ethanol, methanol, isopropanol, dimethylformamide or dimethoxyethane/methanol, at room temperature or above, for example, at reflux temperature, optinally in the presence of an acid acceptor, such as triethylamine.

In the case where an acid addition salt of a compound of formula (II) is used in the reaction, it is preferred that the leaving group ($L_1$) is halogen and that an acid acceptor is present during the course of the reaction. It is even more preferred, however, that the compound of formula (II) is used not in the form of an acid addition salt but in the form of its free base.

In the case where n in the resulting compound of formula (I) is O, the optional oxidation of the compound to obtain another compound of formula (I), wherein n is an integer 1 or 2, may be carried out with a metal, such as sodium, periodate or with one equivalent of m-chloroperbenzoic acid, when n is 1, or with an excess of m-chloroperbenzoic acid, when n is 2. It is preferred, however, that such oxidation is not carried out on a compound of formula (I), wherein X is —S—. It is even more preferred that any oxidation of this kind is carried out at an earlier stage in the process of the invention rather than on a compound of formula (I).

Examples of an optional conversion of $R_1$ in the resulting compound of formula (I) into another $R_1$ include the optional conversion of an aminomethylene group of formula (a), wherein $R_2$ and $R_3$ are hydrogen, into another aminomethylene group of formula (a), wherein $R_2$ or $R_3$ are $C_{1-4}$ alkyl. Such a conversion may be carried out by direct alkylation or by reductive alkylation.

Examples of an optional conversion of $R_4$ and/or $R_5$ in the resulting compound of formula (I) into another $R_4$ and/or $R_5$ include the optional conversion of hydrogen into nitro by nitration, nitro into amino by reduction, halogen into amino by amination, and amino, aminocarbonyl, aminocarbonylamino, amino-thiocarbonylamino and aminosulphonyl into amino, aminocarbonyl, aminocarbonylamino, amino-thiocarbonylamino and aminosulphonyl, the amino group or the amino moiety of the amino-containing groups being substituted by one or two $C_{1-6}$ alkyl, by alkylation or by reductive alkylation. A particularly useful example of an optional conversion of $R_4$ or $R_5$ in the resulting compound of formula (I) into another $R_4$ or $R_5$ is the optional conversion of nitro into amino by reduction, for example, with iron powder and glacial acetic acid.

The optional formation of a pharmaceutically acceptable salt, quaternised derivative, N-oxide or solvate may be carried out conventionally.

The compounds of formula (II) are known, or can be prepared analogously to the preparation of known compounds, for example, from U.S. Pat. Nos. 3,905,984, 4,022,797, 4,053,463, 4,128,658, 4,165,378 and 4,220,654.

The compounds of formula (III) may be prepared from a compound of formula (IV):

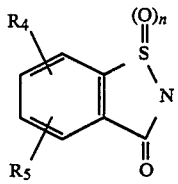
(IV)

wherein $R_4$, $R_5$ and n are as defined hereinbefore, by reaction with a halogenating agent and optionally converting the halogen leaving group ($L_1$) in the resulting compound of formula (III) into another leaving group ($L_1$), or, in the case where $L_1$ is $C_{1-4}$ alkoxy, by reaction with tri $C_{1-4}$ alkoxonium tetrafluoroborate.

Examples of a halogenating agent include thionyl halide, phosphorus oxyhalide and phosphorus pentahalide. A preferred example is phosphorus pentachloride.

The reaction of a compound of formula (IV) and a halogenating agent may be carried out either by heating the reactants in neat form in a high boiling inert solvent, such as decalin, or in an excess of the halogenating agent as solvent optionally in the presence of a tertiary base, such as 2,6-lutidine, to a temperature of 100°-180° C. as appropriate.

The optional conversion of the halogen leaving group ($L_1$) in the resulting compound of formula (III) into another leaving group ($L_1$) may be carried out in accordance with conventional methods. For example, the resulting compound of formula (III) may be reacted with an appropriate $C_{1-4}$ alcohol or $C_{1-4}$ thioalcohol optionally in the presence of an acid halide acceptor, such as pyridine, or in an inert solvent, such as dichloromethane. It is particularly preferred that the compound of formula (IV) is reacted with phosphorus pentachloride and that the resulting compound of formula (III), wherien $L_1$ is chloro, is optionally reacted with a $C_{1-4}$ alcohol, in particular methanol or ethanol.

The compounds of formula (IV) are either known, for example, from U.S. Pat. No. 4,104,387 or Japanese Patents Nos. 590 963 and 656 470, or may be prepared in an analogous manner to the preparation of known compounds.

The present invention provides a second process for preparing a compound of formula (I), wherein X is —S—, —O—,

or —NH, or a pharmaceutically acceptable salt, quaternised derivative, N-oxide or solvate thereof, which comprises reacting a compound of formula (V):

$$R_1-Ar-(CH_2)_a-L_2 \qquad (V)$$

wherein $R_1$, Ar and a are as defined hereinbefore and $L_2$ is a leaving group, with a compound of formula (VI):

$$H-X'-(CH_2)_b-NH-Het \qquad (VI)$$

wherein b and Het are as defined herebefore and X' is —S—, —O—,

or —NH—; in the case where n in the resulting compound of formula (I) is O, optionally oxidising the compound to obtain another compound of formula (I) wherein n is an integer 1 or 2; optionally converting $R_1$, $R_4$ or $R_5$ in the resulting compound of formula (I) into another $R_1$, $R_4$ or $R_5$; and optionally forming a pharmaceutically acceptable salt, quaternised derivative, N-oxide or solvate thereof.

The leaving group ($L_2$) is such as to be displaceable by the compound of formula (VI). Examples of the leaving group ($L_2$) include halogen, such as chloro and bromo, hydroxy, and mesyloxy and tosyloxy.

The reaction between the compounds of formulae (V) and (VI) may be carried out conventionally using either a polar protic or aprotic solvent, in the presence of an acid acceptor, such as triethylamine or a metal carbonate, or in the presence of a strong acid, such as hydrochloric acid.

The optional oxidation may be carried out as described hereinbefore.

Examples of an optional conversion of $R_1$, $R_4$ or $R_5$ include those described hereinbefore.

The optional formation of a pharmaceutically acceptable salt, quaternised derivative, N-oxide or solvate may be carried out as described hereinbefore.

The compounds of formula (V) are either known, for example, from U.K. Patent Application G B. 2,075,980A, Spanish Patent No. 506 422 and *J. Chem. Soc.*, 1958, 4728 to 4731, or may be prepared in an analogous manner to the preparation of known compounds.

The compounds of formula (VI) may be prepared by reacting a compound of formula (III), as defined hereinbefore, with a compound of formula (VII):

$$H-X'-(CH_2)_b-NH_2 \qquad (VII)$$

wherein b and X' are as defined hereinbefore.

The reaction between the compounds of formulae (III) and (VII) may be carried out under the conditions described hereinbefore in relation to the reaction between the compounds of formulae (II) and (III).

The compounds of formula (VII) are known compounds.

The present invention provides a third process for preparing a compound of formula (I), wherein $R_1$ is an aminomethylene group of formula (a), as defined hereinbefore, or a pharmaceutically acceptable salt, quaternised derivative, N-oxide or solvate thereof, which comprises reacting a compound of formula (VIII):

$$L_3CH_2—Ar—(CH_2)_a—X—(CH_2)_b—NH—Het \quad (VIII)$$

wherein Ar, a, X, b and Het are as defined hereinbefore and $L_3$ is a leaving group, with an amine of formula (IX):

wherein $R_2$ and $R_3$ are as defined hereinbefore; in the case where n in the resulting compound of formula (I) is O, optionally oxidising the compound to obtain another compound of formula (I) wherein n is an integer 1 or 2; optionally converting $R_1$, $R_4$ or $R_5$ in the resulting compound of formula (I) into another $R_1$, $R_4$ or $R_5$; and optionally forming a pharmaceutically acceptable salt, quaternised derivative, N-oxide or solvate thereof.

The leaving group ($L_3$) is such as to be displaceable by the amine of formula (IX). Examples of the leaving group ($L_3$) include hydroxy, chloro, bromo, mesyloxy and tosyloxy.

The reaction between the compound of formula (VIII) and the amine of formula (IX) may be carried out under the conditions described hereinbefore in relation to the reaction between the compounds of formulae (V) and (VI).

The optional oxidation may be carried out as described hereinbefore.

Examples of an optional conversion of $R_1$, $R_4$ or $R_5$ include those described hereinbefore.

The optional formation of a pharmaceutically acceptable salt, quaternised derivative, N-oxide, or solvate may be carried out as described hereinbefore.

The compounds of formula (VIII) may be prepared by reacting a compound of formula (III), as defined hereinbefore, with a compound of formula (X):

$$L_3CH_2—Ar—(CH_2)_a—X—(CH_2)_b—NH_2 \quad (X)$$

wherein $L_3$, Ar, a, X and b are as defined hereinbefore.

The reaction between the compounds of formulae (III) and (X) may be carried out under the conditions described hereinbefore in relation to the reaction between the compounds of formulae (II) and (III).

The compounds of formula (X) may be prepared by reacting a compound of formula (XI):

$$L_3'CH_2—Ar—(CH_2)_aL_4 \quad (XI)$$

wherein Ar and a are as defined hereinbefore, $L_3'$ is hydroxy or protected hydroxy and $L_4$ is a preferential leaving group, with a compound of formula (XII):

$$HX—(CH_2)_b—NR_8R_9 \quad (XII)$$

wherein X and b are as defined hereinbefore and $R_8$ and $R_9$ are both hydrogen, or one of $R_8$ and $R_9$ is hydrogen and the other is a protecting group, or both of $R_8$ and $R_9$ together are a protecting group; in the case where in the resulting compound $L_3$ is protected hydroxy, removing the protecting group; optionally converting the hydroxy leaving group ($L_3$) in the resulting compound into another leaving group ($L_3$); and in the case where in the resulting compound one of $R_8$ and $R_9$ or both of $R_8$ and $R_9$ together are a protecting group, removing the protecting group.

Examples of the group ($L_3'$), when protected hydroxy, include tetrahydropyranyl.

The preferential leaving group ($L_4$) is such as to be displaceable (in preference to the group ($L_3'$)) by the compound of formula (XII). Examples of the preferential leaving group ($L_4$) include chloro, bromo, hydroxy, mesyloxy and tosyloxy. When $L_4$ is hydroxy and a is other than 1, it is preferred that $L_3'$ is protected hydroxy.

In the case where one of $R_8$ and $R_9$ is hydrogen and the other is a protecting group, examples of a protecting group include $C_{1-4}$ alkanoyl.

In the case where both of $R_8$ and $R_9$ together are a protecting group, examples of a protecting group include phthalimidyl.

The reaction between the compounds of formulae (XI) and (XII) may be carried out under the conditions described hereinbefore in relation to the reaction between the compounds of formulae (V) and (VI).

The removal of a protecting group from the resulting compound, wherein the group ($L_3'$) is protected hydroxy, may be carried out conventionally.

The optional conversion of the hydroxy leaving group ($L_3$) into another leaving group ($L_3$) may be carried out as described hereinbefore in relation to the leaving group ($L_1$).

The removal of a protecting group from the resulting compound, wherein one of or both together of $R_8$ and $R_9$ are a protecting group, may be carried out conventionally.

The present invention provides a fourth process for preparing a compound of formula (I), wherein $R_1$ is an aminomethylene group of formula (a), as defined hereinbefore, or a pharmaceutically acceptable salt, quaternised derivative, N-oxide or solvate thereof, which comprises reacting a compound of formula (XIII):

$$H—Ar—(CH_2)_a—X—(CH_2)_b—NH—Het \quad (XIII)$$

wherein Ar, a, X, b and Het are as defined hereinbefore, with formaldehyde and a compound of formula (IX), as defined hereinbefore; in the case where n in the resulting compound of formula (I) is O, optionally oxidising the compound to obtain another compound of formula (I) wherein n is an integer 1 or 2; optionally converting $R_1$, $R_4$ or $R_5$ in the resulting compound of formula (I) into another $R_1$, $R_4$ or $R_5$; and optionally forming a pharmaceutically acceptable salt, quaternised derivative, N-oxide or solvate thereof.

The reaction between the compounds of formulae (XIII) and (IX) and formaldehyde is a Mannich reaction and may be carried out under conventional Mannich reaction conditions, for example, in aqueous media in the presence of a strong acid, such as hydrochloric acid.

The optional oxidation may be carried out as described hereinbefore.

Examples of an optional conversion of $R_1$, $R_4$ or $R_5$ include those described hereinbefore.

The optional formation of a pharmceutically acceptable salt, quaternised derivative, N-oxide or solvate may be carried out as described hereinbefore.

The compound of formula (XIII) may be prepared by reacting a compound of formula (III), as defined hereinbefore, and a compound of formula (XIV):

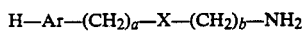

$$H-Ar-(CH_2)_a-X-(CH_2)_b-NH_2 \quad (XIV)$$

wherein Ar, a, X and b are as defined hereinbefore.

The reaction between the compounds of formulae (III) and (XIV) may be carried out under conditions described hereinbefore in relation to the reaction between the compounds of formulae (II) and (III).

The compounds of formula (XIV) may be prepared by reacting a compound of formula (XV):

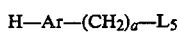

$$H-Ar-(CH_2)_a-L_5 \quad (XV)$$

wherein Ar and a are as defined hereinbefore and $L_5$ is a leaving group, with a compound of formula (XII), as defined hereinbefore; in the case where in the resulting compound one of $R_8$ and $R_9$ or both of $R_8$ and $R_9$ together are a protecting group, removing the protecting group.

The leaving group ($L_5$) is such as to be displaceable by the compound of formula (XII). Examples of the leaving group ($L_5$) include chloro, bromo, hydroxy, mesyloxy and tosyloxy.

The reaction between the compounds of formulae (XV) and (XII) may be carried out under the conditions as described hereinbefore in relation to the reaction between the compounds of formulae (V) and (VI).

The compounds of formulae (III), (VI), (VIII) and (XIII) are novel intermediates and represent part of the present invention. A sub-class of such novel intermediates is of formulae (III), (VI), (VIII) and (XIII), $R_4$ being hydrogen and $R_5$ being as defined hereinbefore in the 4-position. A preferred sub-class is of formulae (III), (VI), (VIII) and (XIII), $R_4$ being hydrogen and $R_5$ being nitro or amino in the 4-position.

As mentioned hereinbefore, the compounds of formula (I), and their pharmaceutically acceptable salts, quaternised derivatives, N-oxides and solvates thereof, are histamine $H_2$-receptor antagonists and, therefore, are able to inhibit gastric acid secretion. In this way, the compounds may be used in the treatment or prophylaxis of any disorder caused or exacerbated by excess gastric acid secretion, such as peptic ulcers.

Accordingly, the present invention also provides a pharmaceutical composition, which comprises a compound of formula (I), as defined hereinbefore, or a pharmaceutically acceptable salt, quaternised derivative, N-oxide or solvate thereof, and a pharmaceutically acceptable carrier.

The composition of the present invention may be formulated for administration by any route, although in general oral administration is preferred. The composition may be in the form of a tablet, capsule, powder, granule, lozenge, suppository, reconstitutable powder, or a liquid preparation, such as an oral or sterile parenteral solution or suspension.

In order to obtain consistency of administration it is preferred that a composition of the invention is in the form of a unit dose.

Unit dose presentation forms for oral administration may take the form of a tablet or a capsule and may contain conventional excipients such as a binding agent, for example syrup, acacia, gelatin, sorbitol, tragacanth, or polyvinyl-pyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions of the present invention may be prepared by conventional methods of blending, filling, tabletting or the like. Repeated blending operations may be caused to distribute the active agent throughout those compositions employing large quantities of fillers.

Such operations are of course conventional in the art. The tablets may be coated according to methods well known in normal pharmaceutical practice.

A particular composition of the invention is a tablet containing the required amount of a compound of the invention in the form of a powder or granulate compressed in intimate mixture with a lubricant, such as magnesium stearate, a filler, such as microcrystalline cellulose, and a disintegrant, such as sodium starch glycollate.

Oral liquid preparations may be in the form of, for example, an emulsion, syrup, or elixir, or may be presented as a dry product for reconstitution with water or other suitable vehicle before use. Such liquid preparations may contain conventional additives such as a suspending agent, for example sorbitol, syrup, methyl cellulose, gelatin, hydroxyethylcellulose, carboxymethylcellulose, aluminium stearate gel, hydrogenated edible fats; and emulsifying agent, for example lecithin, sorbitol monooleate, or acacia; a non-aqueous vehicle (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and a buffering agent can be dissolved in the vehicle. To enhance the stability, the composition can be frozen after filling into the vial and the water removed under vacuum. Parenteral suspensions are prepared in substantially the same manner, except of course that the compound is suspended in the vehicle instead of being dissolved, and sterilization cannot be accomplished by filtration. However, the compound can be sterilized by exposure to ethylene oxide before suspending in the sterile vehicle. Advantageously, a surfactant or wetting agent is included in the composition to facilitate uniform distribution of the compound.

When appropriate the composition of the invention may be presented as a suppository for rectal or vaginal administration. Suitable unit dose forms include tablets, capsules and powders in sachets or vials, and preferred forms include shaped oral unit doses, such as tablets and capsules.

The compositions may contain from 0.1% to 99% by weight, preferably from 10–60% by weight, of the active material, depending on the method of administration.

It will be appreciated of course that the quantity of the compound administered to the sufferer each day will depend on the usual factors such as the severity of the disease, and the weight of the sufferer and on the dose-response characteristics of the particular active ingredient. Suitably however it is believed that between 0.1 to 25 mg/kg/day of the compound will be administered to achieve satisfactory therapy. Such administration is conveniently effected with repeated dosing throughout the day of the composition in unit dose form.

By way of example, unit dose compositions will suitably contain from 5 to 2000 mg, more preferably from 10 to 1000 mg of the active ingredient.

The invention also provides a method of treatment or prophylaxis of disorders, such as peptic ulcers, in mammals including humans, caused or exacerbated by excess gastric acid secretion, which method comprises the administration to the mammal of an effective amount of the compound of formula I, as hereinbefore defined, or a pharmaceutically acceptable salt, quaternised derivative, N-oxide or solvate thereof.

The following Examples illustrate the compounds of the present invention.

DESCRIPTION 1

Preparation of
3-chloro-4-nitro-1,2-benzoisothiazole-1,1-dioxide

(D1a)

An intimate mixture of 4-nitrosaccharin [0.50 g, prepared as described by G. H. Hamor, *J. Amer. Pharm. Soc.*, 49, 280 (1960)] and phosphorus pentachloride was heated at 180° C. for 1.5 hours. The phosphorus oxychloride formed was removed by distillation and the dark residue was partitioned between water (50 ml) and dichloromethane (2×50 ml). The combined organic phase was washed with brine (2×70 ml) and dried over magnesium sulphate. Removal of solvent in vacuo gave an amorphous orange residue (0.43 g) which was used without further purification. A sample was triturated under ether to yield a white solid mpt. 203°–5° C.

Prepared analogously were:
3-chlorobenzoisothiazole-1,1-dioxide (D1b)
3,4-dichlorobenzoisothiazole-1,1-dioxide (D1c)
3-chloro-5-nitrobenzoisothiazole-1,1-dioxide (D1d)
3-chloro-6-nitrobenzoisothiazole-1,1-dioxide (D1e)
3-chloro-7-nitrobenzoisothiazole-1,1-dioxide (D1f)
3,6-dichlorobenzoisothiazole-1,1-dioxide (D1g)
3-chloro-6-dimethylsulphamoyl-benzoisothiazole-1,1-dioxide (D1h)
3-chloro-4-methylbenzoisothiazole-1,1-dioxide (D1i)
3-chloro-4-iodobenzoisothiazole-1,1-dioxide (D1j)
3-chloro-4-cyanobenzoisothiazole-1,1-dioxide (D1k)

DESCRIPTION 2a

3-Ethoxy-4-nitro-benzoisothiazole-1,1-dioxide

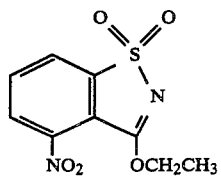
(D2a)

Ethanol (100 ml) was added to a solution of 3-chloro-4-nitro-benzoisothiazole-1,1-dioxide (0.86 g) in dichloromethane (110 ml). The resulting solution was allowed to stand overnight at room temperature. Removal of the solvent in vacuo gave an amorphous brown solid, which was triturated under ether (100 ml) to give the title compound as a white solid (0.82 g), mpt 190°–191° C.

$^1$H-NMR: CDCl$_3$-d$^6$-DMSO; δ=1.33 (t, 3H), δ=4.47 (q, 2H), δ=7.95–8.34 (m, 3H).

DESCRIPTION 2b

3-Ethoxy-6-nitro-benzoisothiazole-1,1-dioxide

(D2b)

Following the procedure outlined in Description 2a, 3-chloro-6-nitro-benzoisothiazole-1,1-dioxide (4.2 g) was converted to the title compound (4.3 g).

$^1$H-NMR: CDCl$_3$; δ=1.56 (t, 3H), δ=4.66 (q, 2H), δ=7.96 (d, 1H), δ=8.4–8.75 (m, 2H).

DESCRIPTION 2c

3-Ethoxy-5-nitro-benzoisothiazole-1,1-dioxide

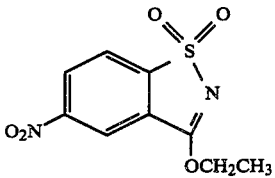
(D2c)

Following the procedure outlined in Description 2a, 3-chloro-5-nitro-benzoisothiazole-1,1-dioxide (2.9 g) was converted to the title compound (2.4 g) mp. 151°–4°

$^1$H-NMR: CDCl$_3$-d$^6$ DMSO; δ=1.55 (t, 3H), δ=4.62 (q, 2H), δ=8.08 (d, 1H, J=8.5 Hz), δ=8.35–8.7 (m, 2H).

DESCRIPTION 2d

3-Ethoxy-4-methyl-benzoisothiazole-1,1-dioxide

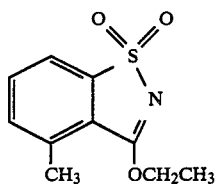
(D2d)

Following the procedure outlined in Description 2a, 3-chloro-4-methyl-benzoisothiazole-1,1-dioxide was converted to the title compound.

$^1$H-NMR: d$_6$-DMSO; δ=1.52 (t, 3H), δ=2.65 (s, 3H), δ=4.60 (q, 2H), δ=7.5–8.15 (m, 3H).

DESCRIPTION 2e

3-Ethoxy-6-dimethylsulphamoylbenzoisothiazole-1,1-dioxide

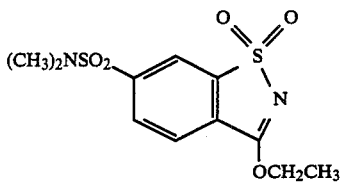
(D.2e)

Following the procedure outlined in Description 2a, 3-chloro-6-dimethylsulphamoylbenzoisothiazole-1,1-dioxide (D1h) was converted to the title compound.

$^1$H-NMR: CDCl$_3$+CD$_3$OD; δ=1.55 (t, 3H), δ=2.76 (s, 6H), δ=4.66 (q, 2H), δ=7.7–8.3 (m, 3H).

The following 3-ethoxy-6-sulphamoylbenzoisothiazole-1,1-dioxides were prepared similarly.
3-Ethoxy-6-methylsulphamoylbenzoisothiazole-1,1-dioxide (D.2f).

DESCRIPTION 3a

4-Amino-3-ethoxy-benzoisothiazole-1,1-dioxide

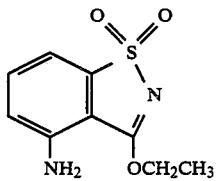
(D3a)

A solution of 3-ethoxy-4-nitro-benzoisothiazole-1,1-dioxide (0.81 g) in ethanol (250 ml) in the presence of 5% Pd-carbon (0.2 g) was hydrogenated at atmospheric pressure and ambient temperature until the theoretical volume of hydrogen had been taken up.

The mixture was filtered through Kieselguhr and the residue washed thoroughly with methanol. Removal of solvent in vacuo gave the title compound as a pale yellow solid (0.63 g) mpt 213°–216° C. (dec).

$^1$H-NMR: d$^6$-DMSO, CDCl$_3$; δ=1.43 (t, 3H), δ=4.48 (q, 2H), δ=6.26 (br.s. 2H), δ=6.7–6.96 (m, 2H), δ=7.13–7.5 (m, 1H).

DESCRIPTION 3b

6-Amino-3-ethoxy-benzoisothiazole-1,1-dioxide

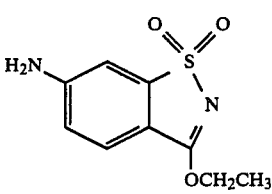
(D3b)

Following the procedures outlined in Description 3a, 3-ethoxy-6-nitro-benzoisothiazole-1,1-dioxide (4.3 g) was converted to the title compound (2,4 g).

$^1$H-NMR: d$^6$-DMSO-CDCl$_3$ δ=1.42 (t, 3H), δ=4.45 (d, 2H), δ=5.4–6.9 (br.s. 2H), δ=6.5–7.0 (m, 2H), δ=7.3 (d, 1H).

Mass spectrum: C$_9$H$_{10}$N$_2$O$_3$S—Required 226.0412, Observed 226.0411.

DESCRIPTION 3c

5-Amino-3-ethoxy-benzoisothiazole-1,1-dioxide

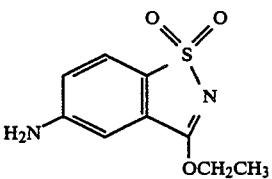
(D3c)

Following the procedures outlined in Description 3a 3-ethoxy-5-nitro-benzoisothiazole-1,1-dioxide (2.3 g) was converted to the title compound (0.95 g).

mp: 154°–6°.

$^1$H-NMR: CDCl$_3$-d$^6$DMSO; δ=1.43 (t, 3H), δ=4.45 (q, 2H), δ=6.8–7.1 (m, 2H), δ=7.52 (d, 1H, J=9 Hz); δ=8–8.4 (brs, 2H exchangeable with D$_2$O).

DESCRIPTION 4a

6-Acetamido-3-ethoxy-benzoisothiazole-1,1-dioxide

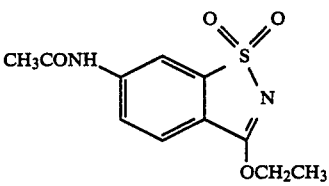
(D4)

A solution of 6-amino-3-ethoxy-benzoisothiazole-1,1-dioxide (0.23 g) and acetic anhydride (0.1 ml) in pyridine (1 ml) was stirred at room temperature for 15 hrs. Concentration and trituration under ether/petrol (1:1) gave the title compound (0.24 g).

$^1$H-NMR: d$^6$DMSO-CDCl$_3$; δ=1.50 (t, 3H), δ=2.17 (s, 3H), δ=4.62 (q, 2H), δ=7.5–8.0 (m, 2H), δ=8.37 (d, 1H), δ=10.5 (br.s. 1H).

Mass spectrum: C$_{11}$H$_{12}$N$_2$O$_4$S—Required: 268.0518, Observed: 268.0511.

DESCRIPTION 4b

6-Methylcarbamoylamino-3-ethoxy-benzoisothiazole-1,1-dioxide

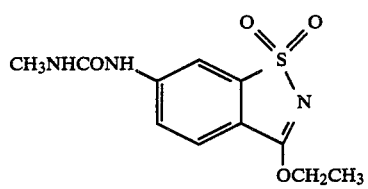

Following the procedures outlined in Description 4a, 6-amino-3-ethoxy-benzoisothiazole-1,1-dioxide (0.23 g) was reacted with methyl isocyanate for 3 days to give the title compound.

$^1$H-NMR: $CDCl_3 + d_6 DMSO$; $\delta = 1.5$ (t, 3H), $\delta = 2.7$, 2.76 (2S, 3H), $\delta = 4.53$ (q, 2H), $\delta = 7.3-8.1$ (m, 2H), $\delta = 8.16$ (brs, 1H).

Mass spectrum: $C_{11}H_{13}N_3O_3S$—Required: 283.0627, Observed: 283.0626.

DESCRIPTION 4c

6-Methanesulphamoylamino-3-ethoxy-benzoisothiazole-1,1-dioxide

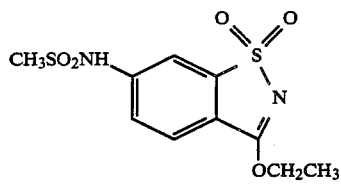

Following the procedures outlined in Description 4a, 6-amino-3-ethoxy-benzoisothiazole-1,1-dioxide was reacted with methane sulphonyl chloride to give the title compound.

DESCRIPTION 4d

6-Propionamido-3-ethoxy-benzoisothiazole-1,1-dioxide

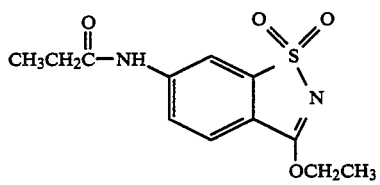

Following the procedures outlined in Description 4a, 6-amino-3-ethoxy-benzoisothiazole-1,1-dioxide was reacted with propionic anhydride to give the title compound.

mp. 188°–92°.

$^1$H-NMR: $CDCl_3 + CD_3OD$; $\delta = 1.25$ (t, 3H), $\delta = 1.55$ (t, 3H), $\delta = 2.47$ (q, 2H), $\delta = 4.65$ (q, 2H), $\delta = 7.35-8.25$ (m, 3H).

Mass spectrum: $C_{12}H_{14}N_2O_4S$—Required: 282.0674, Observed: 282.0682.

DESCRIPTION 4e

6-Formamido-3-ethoxy-benzoisothiazole-1,1-dioxide

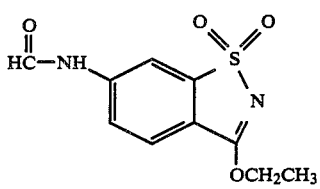

Following the procedures outlined in Description 4a, 6-amino-3-ethoxy-benzoisothiazole-1,1-dioxide was reacted with formic-acetic anhydride to give the title compound.

mp. 188°–94°.

$^1$H-NMR: $CDCl_3 + CD_3OD$; $\delta = 1.52$ (t, 3H), $\delta = 4.65$ (q, 2H), $\delta = 7.6-8.1$ (m, 2H), $\delta = 8.25$ (brs, 1H), $\delta = 8.42$ (s, 1H).

Mass spectrum: $C_{10}H_{10}N_2O_4S$—Required: 254.0362, Observed: 254.0366.

DESCRIPTION 5

5,6-Dimethoxy-3-ethoxy-benzoisothiazole-1,1-dioxide

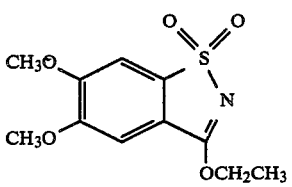

To a solution of 5,6-dimethoxysaccharin (0.8 g) in dichloromethane (100 ml) was added triethyloxonium tetrafluoroborate (3.5 ml, 1M soln in $CH_2Cl_2$) and the solution stirred at room temperature for 3 hrs. After extraction with aqueous sodium bicarbonate, the organic phase was dried and concentrated. Purification by column chromatography (silica, chloroform) gave the title compound (0.2 g).

$^1$H-NMR: $CDCl_3$; $\delta = 1.5$ (t, 3H), $\delta = 3.92$ (s, 6H), $\delta = 4.53$ (q, 2H), $\delta = 6.97$ (s, 1H), $\delta = 7.23$ (s, 1H).

DESCRIPTION 6

Preparation of 6-dimethylsulphamoyl saccharin

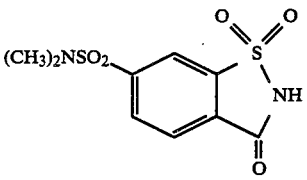

A suspension of 6-aminosaccharin (1 g) in glacial acetic acid (8 ml), conc. hydrochloric acid (4 ml) and water (3 ml) was diazotised with a solution of sodium nitrite (0.37 g) in water (1 ml) at 0°–10° for 1 h. The diazonium salt solution was poured into a solution of cupric chloride (1 g) in water (2.5 ml), glacial acetic acid (20 ml) and sulphur dioxide (12 g) and the mixture was stirred at room temperature for 1 h. On pouring into ice, the crude sulphonyl chloride which precipitated was collected and dried (0.5 g, mp 191°–3°).

The sulphonyl chloride was dissolved in alcoholic dimethylamine (33% v/v, 15 ml) and stirred overnight at room temperature. On evaporation of the solvent, water trituration yielded the title compound (0.4 g) mp 198°-200°.

'H-NMR; d⁶ DMSO; δ=2.70 (s, 6H), δ=8.25 (br s, 2H), δ=8.40 (br s, 1H).

mass spectrum: $C_9H_{10}N_2O_5S_2$—Required: 290.0032, Observed: 290.0040.

DESCRIPTION 7

N-[3-(3-Piperid-1-ylmethylphenoxy)propyl]-1,2-benzoisothiazole-3-amine

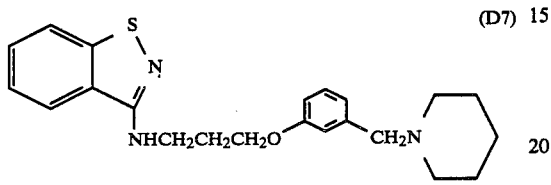
(D7)

was prepared by the method of Example 13 using DMF as the solvent and potassium carbonate as the base with heating under reflux for 1 hour.

¹H-NMR: $CDCl_3+D_2O$; δ=1.2-1.8 (m, 6H), δ=2.0-2.6 (m, 6H), δ=3.43 (s, 2H), δ=3.80 (t, 2H), δ=4.15 (t, 2H), δ=6.7-7.9 (m, 8H).

Mass spectrum: $C_{22}H_{27}N_3OS$—Required: 381.1874, Observed: 381.1875.

DESCRIPTION 8

Preparation of 6-iodo-3-ethoxy-benzoisothiazole-1,1-dioxide

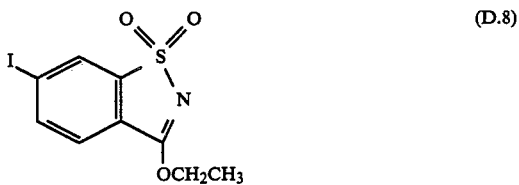
(D.8)

6-Amino-3-ethoxybenzoisothiazole-1,1-dioxide (D.3b) (0.25 g) was diazotised with sodium nitrite (0.21 g) in conc. sulphuric acid (5 ml) at 0°-10° C. for 2 h. After pouring into an aqueous (50 ml) solution of potassium iodide (1 g), the black suspension was treated with sodium metabisulphite until an orange precipitate remained. The solid was collected, washed with water and dried (0.26 g, mp 185°-90°)

¹H NMR: δ=1.28 (t, 3H), δ=4.34 (q, 2H), δ=7.12 (d, 1H), δ=7.75 (dd, 1H), δ=7.90 (brs, 1H).

DESCRIPTION 9

N³-[2-Mercapto ethyl]-1,2-benzoisothiazole-3,4-diamine-1,1-dioxide

(D.9)

Following the procedures outlined in Example 17, but using cysteamine, 2-methoxyethanol as solvent and at room temperature for 3 days, the title compound was obtained after evaporation to dryness and trituration with methanol.

¹H NMR:d⁶DMSO; δ2.0-3.2 (m, 2H), 3.5-3.9 (m, 2H), 2.9-3.9 (m, 1H exchanges with $D_2O$), 6.2-6.7 (m, 2H exchanges with $D_2O$), 6.9-7.2 (m, 1H) 7.2-7.5 (m, 1H).

EXAMPLE 1

Preparation of N-[2-(5-dimethylaminomethylfuran-2-ylmethylthio)ethyl]4-nitro-1,2-benzoisothiazole-3-amine-1,1-dioxide

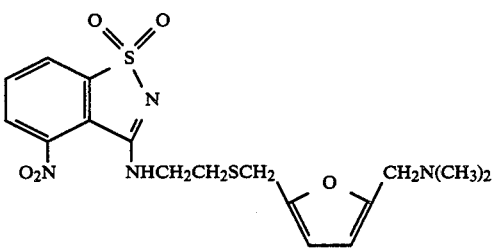

A solution of 4-nitropseudosaccharin chloride (0.43 g, 0.00175 mole) in dichloromethane (10 ml) was added dropwise to a stirred solution of 2-[(5-dimethylaminomethylfuran-2-yl)methylthio]ethylamine (0.41 g, 0.00192 mole) and triethylamine (0.177 g, 0.00175 mole) in dichloromethane (10 ml) at ambient temperature. The mixture was stirred for 16 hours and was then transferred to a separating funnel and washed with water. The aqueous phase was extracted with dichloromethane (50 ml). The combined organic phase was washed with brine (2×75 ml), dried over magnesium sulphate and evaporated under reduced pressure. The residual crude product was purified, via chromatography on silica gel using 5% methanol chloroform as eluant, to yield the title compound as an orange oil (0.28 g) which solidified on standing to yield orange crystals, mpt. 115°-6° C.

¹H-NMR: $CDCl_3$ 79.5 MHz; δ=2.27 (s, 6H), δ=2.90 (t, 2H), δ=3.48 (s, 2H), δ=3.65-3.95 (m, 4H), δ=6.1-6.25 (m, 2H), δ=7.9-8.5 (m, 3H), δ=8.75 (br s, 1H).

Mass spectrum: $C_{17}H_{20}N_4O_2S_2$—Required: 424.0873, Observed: 424.0864.

EXAMPLE 2

Preparation of N³-[2-(5-dimethylaminomethylfuran-2-ylmethylthio)ethyl]1,2-benzoisothiazole-3,4-diamine-1,1-dioxide

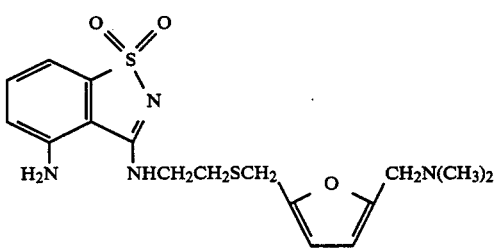

A mixture of electrolytic iron powder (0.080 g, N-[2-(5-dimethylaminomethylfuran-2-ylmethylthio)ethyl]1,2-benzothiazole-3-amine 1,1-dioxide (0.170 g), glacial acetic acid (0.50 ml) and ethanol (10 ml) was vigorously stirred under reflux for 2.5 hours. Sodium bicarbonate solution was then added to neutralise the mixture and the mixture was extracted with chloroform (2×20 ml). The combined organic phase was washed with brine (20 ml), dried over magnesium sulphate and evaporated under reduced pressure. The crude residual product was purified by chromatography on alkaline alumina (Brockman type II) using chloroform as eluent to yield the title compound as a yellow gum which solidified on standing to give a white solid, mp 88°–90° C., (ethanol/water).

'H-NMR: CDCl₃ 79.5 MHz; δ=2.19 (s, 6H), δ=2.75 (t, 2H); δ=3.3—3.5 (m, 4H including 3.36, s), δ=3.73 (s, 2H), δ=4.2–5.3 (br s, 3H), δ=6.05–6.2 (2d, 2H), δ=6.9–7.2 (dd, 1H), δ=7.25–7.6 (m, 2H).

Mass spectrum: $C_{17}H_{22}N_4O_4S$—Required: 394.1132, Observed: 394.1134.

By means of similar procedures to those outlined in Example 1, the following compounds were prepared. The solvents and reaction times were varied as required.

EXAMPLE 3

N-[2-(5-dimethylaminomethylfuran-2-ylmethylthio)ethyl]-1,2-benzoisothiazole-3-amine-1,1-dioxide

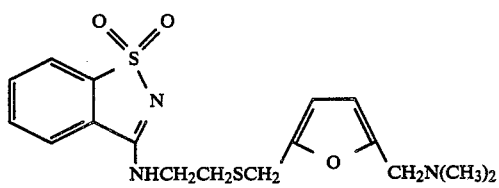

mp. 95°–8°.

'H—NMR: CDCl₃; δ=2.25 (s, 6H), δ=2.85 (t, 2H), δ=3.1–3.95 (m, 7H, 1H exchangeable with D₂O), δ=6.2 (2d, 2H), δ=7.5–8.0 (m, 5H, 1H exchangable with D₂O).

Mass spectrum: $C_{17}H_{21}N_3O_3S_2$—Required: 379.1024, Observed: 379.1002.

EXAMPLE 4

N-[2-(5-dimethylaminomethylfuran-2-ylmethylthio)ethyl]-4-chloro-1,2-benzoisothiazole-3-amine-1,1-dioxide

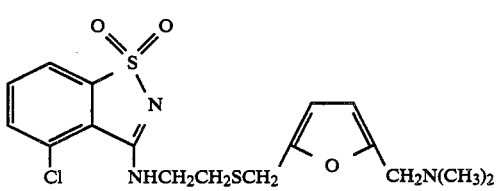

mp. 109°–10°.

'H NMR: CDCl₃; δ=2.22 (s, 6H), δ=2.87 (t, 3H), δ=3.40 (s, 2H), δ=3.7–4.0 (m, 4H including 3.77, s), δ=6.0–6.3 (2d, 2H), δ=7.55–8.0 (m, 4H).

Mass spectrum: $C_{17}H_{20}Cl\ N_3O_3S_2$—Required: 413.0643, Observed: 413.0635.

EXAMPLE 5

N-[2-(5-dimethylaminomethylfuran-2-ylmethylthio)ethyl]5-nitro-1,2-benzoisothiazole-3-amine-1,1-dioxide

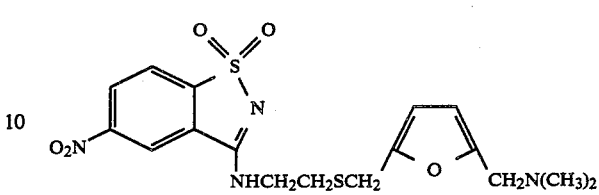

'H NMR: CDCl₃; δ=2.38 (s, 6H), δ=2.90 (t, 2H), δ=3.25–3.80 (m, 6H including 3.58, s; 3.75, s), δ=3.85–4.90 (br s, 1H exchangeable with D₂O), δ=6.05–6.30 (2d, 2H), δ=7.95–9.00 (m, 4H; 1H exchangeable with D₂O).

Mass spectrum: $C_{17}H_{20}N_4O_5S_2$—Required: 424.0875, Observed: 424.0876.

EXAMPLE 6

N-[2-(5-dimethylaminomethylfuran-2-ylmethylthio)ethyl]-6-nitro-1,2-benzoisothiazole-3-amine-1,1-dioxide

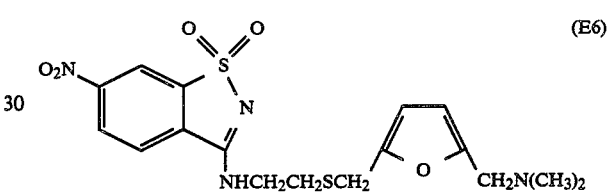

(E6)

1H-NMR: CDCl₃; δ=2.23 (s, 6H), δ=2.82 (t, 2H), δ=3.43 (s, 2H), δ=3.58–3.88 (m, 4H), δ=6.1 (s, 2H), δ=6.4–7.8 (br s, 1H), δ=7.96–8.86 (m, 3H).

EXAMPLE 7

N-[2-(5-dimethylaminomethylfuran-2-ylmethylthio)ethyl]-7-nitro-1,2-benzoisothiazole-3-amine-1,1-dioxide

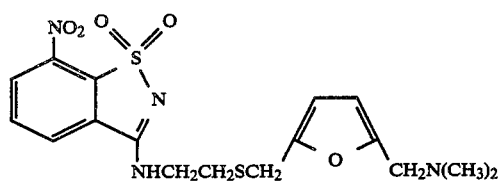

'H NMR: CDCl₃; δ=2.37 (s, 6H), δ=2.89 (t, 3H), δ=3.3–3.8 (m, 7H including 3.58, s and 3.75, s), δ=6.24 (s, 2H), δ=7.8–8.05 (m, 1H), δ=8.35–8.65 (m, 2H).

EXAMPLE 8

N-[2-(5-dimethylaminomethylfuran-2-ylmethylthio)ethyl]-6-chloro-1,2-benzoisothiazole-3-amine-1,1-dioxide

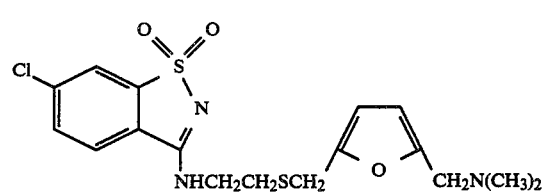

'H NMR: CDCl₃; δ=2.37 (s, 6H), δ=2.86 (t, 2H), δ=3.35–3.85 (m, 6H including 3.59, s and 3.76, s), δ=4.25–5.25 (br s, 1H), δ=6.1–6.3 (2d, 2H), δ=7.5–8.10 (m, 3H).

Mass spectrum: $C_{17}H_{20}Cl\ N_3O_3S_2$—Required: 413.0635, Observed: 413.0625.

EXAMPLE 9

N-[2-(5-Dimethylaminomethylfuran-2-ylmethylthio)ethyl]-6-dimethylsulphamoyl-1,2-benzoisothiazole-3-amine-1,1-dioxide

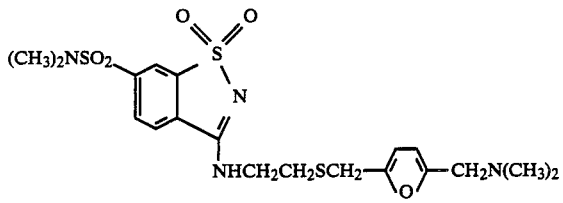

mp. 155°–8° (dec).

¹H NMR: CDCl₃; δ=2.25 (s, 6H), δ=2.78 (s, 6H), δ=2.87 (t, 2H), δ=3.45 (s, 3H), δ=3.57 (t, 2H), δ=3.76 (s, 2H), δ=6.19 (dd, 2H), δ=8.06 (m, 2H), δ=8.24 (m, 1H), δ=7.2–8.5 (brs, 1H).

Mass spectrum: $C_{19}H_{26}N_4O_5S_3$—Required: 486.1065, Observed: 486.1069.

EXAMPLE 10

N-[3-(3-piperid-1-ylmethylphenoxy)propyl]-1,2-benzoisothiazole-3-amine-1,1-dioxide

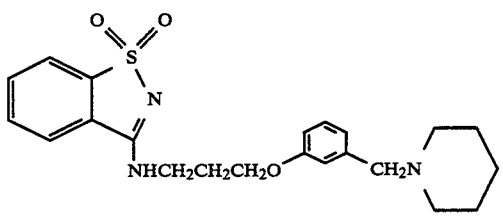

mp. 140°–2°.

'H NMR: CDCl₃; δ=1.3–1.8 (m, 6H), δ=2.0–2.55 (m, 6H), δ=3.48 (s, 2H), δ=3.65–3.95 (br t, 2H), δ=4.13 (t, 2H), δ=6.55–6.7 (m, 5H), δ=7.55–8.0 (m, 4H).

Mass spectrum: $C_{22}H_{27}N_3O_3S$—Required: 413.1773, Observed: 413.1769.

EXAMPLE 11

N-[3-(3-piperid-1-ylmethylphenoxy)propyl]-4-nitro-1,2-benzoisothiazole-3-amine-1,1-dioxide

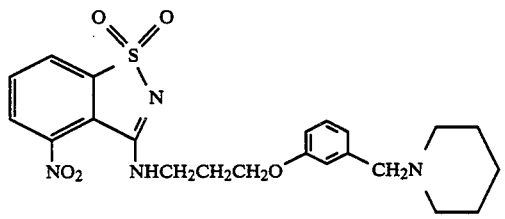

mp. 143°–5° (dec).

'H NMR: CDCl₃; δ=1.25–1.8 (m, 6H), δ=2.05–2.6 (m, 6H), δ=3.49 (s, 2H), δ=3.92 (t, 2H), δ=4.06 (t, 2H), δ=6.7–7.07 (m, 3H), δ=7.07–7.37 (m, 1H), δ=7.78–8.1 (m, 2H), δ=8.15–8.45 (m, 1H), δ=8.3–9.0 (m, 1H).

Mass spectrum: $C_{22}H_{26}N_4O_5S$—Required: 458.1624, Observed: 458.1627.

EXAMPLE 12

N-[3-(3-dimethylaminomethylphenoxy)propyl]-1,2-benzoisothiazole-3-amine-1,1-dioxide

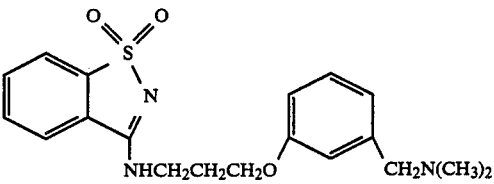

mp. 126°–9°.

'H-NMR: CDCl₃; δ=2–2.5 (m, 8H including 2.25, s), δ=3.42 (s, 2H), δ=3.6–3.95 (br q, 2H, collapses to t with D₂O), δ=4.14 (t, 2H), δ=6.65–7.55 (m, 5H, to 4H with D₂O), δ=7.55–8.0 (m, 4H).

Mass spectrum: $C_{19}H_{23}N_3O_3S$—Requirred: 373.1460, Observed: 373.1470.

EXAMPLE 13

N-[2-(2-guanidinothiazol-4-ylmethylthio)ethyl]-4-nitro-1,2-benzoisothiazole-3-amine-1,1-dioxide

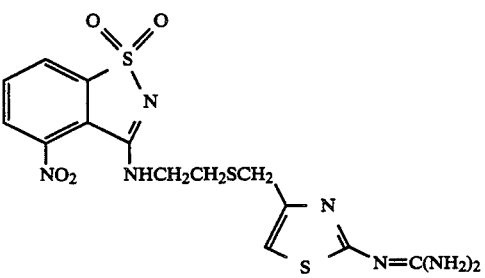

mp. 190°–1° (dec).

'H-NMR: d⁶DMSO; δ=2.8 (t, 2H), δ=3.5–3.95 (m, 4H including 3.7, s), δ=6.6 (s, 1H), δ=6.5–7.25 (br s, 4H exchanges with D₂O), δ=7.85–8.25 (m, 1H), δ=8.3–8.55 (m, 2H), δ=8.45–9.15 (br s, 1H exchanges with D₂O).

Mass spectrum: $C_{14}H_{15}N_7O_4S_3$—Required: 441.0349, Observed: 441.0318.

EXAMPLE 13a

N-[2-(5-Dimethylaminomethylfuran-2-ylmethylthio)ethyl]-4-iodo-1,2-benzoisothiazole-3-amine-1,1-dioxide

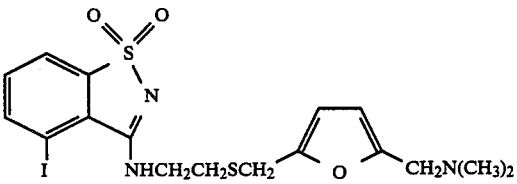

¹H-NMR: CDCl₃; δ=2.25 (s, 6H), δ=2.90 (t, 2H), δ=3.42 (s, 2H), δ=3.6–4.0 (m, 4H including 3.80, s, 2H), δ=6.0–6.25 (2d, 2H), δ=7.2–8.25 (m, 4H, 1H exchangeable with D₂O).

Mass spectrum: $C_{17}H_{20}N_3O_3S_2I$—Required: 504.9992, Observed: 504.9985.

EXAMPLE 13b

N-[2-(5-Dimethylaminomethylfuran-2-ylmethylthio)ethyl]-4-cyano-1,2-benzoisothiazole-3-amine-1,1-dioxide

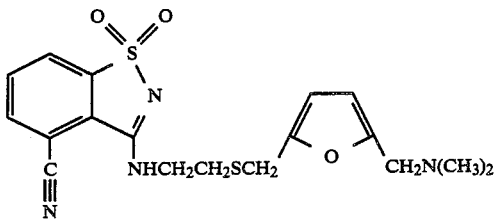

¹H-NMR: CDCl₃; δ=2.25 (s, 6H), δ=2.90 (t, 2H), δ=3.44 (s, 2H), δ=3.6–4.0 (m, 4H including 3,8, s, 2H), δ=6.05–6.25 (2d, 2H), δ=7.5–8.25 (m, 3H), δ=7.2–8.4 (br m, 1H exchangeable with D₂O).

Mass spectrum: C₁₈H₂₀N₄O₃S₂—Required: 404.0977 Observed: 404.0954.

By means of similar procedures to those outlined in Example 2, the following compounds were prepared. 5N Hydrochloric acid was frequently used in place of glacial acetic acid.

EXAMPLE 14

N³-[2-(5-dimethylaminomethylfuran-2-ylmethylthio)ethyl]-1,2-benzoisothiazole-3,6-diamine-1,1-dioxide

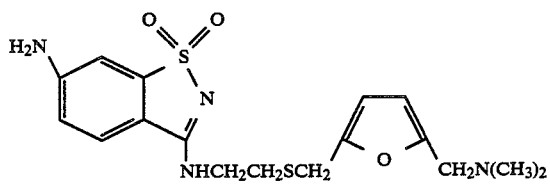

Mass spectrum: C₁₇H₂₂N₄O₃S₂—Required: 394.1133, Observed: 394.1130.

EXAMPLE 15

N³-[2-(5-dimethylaminomethylfuran-2-ylmethylthio)ethyl]-1,2-benzoisothiazole-3,7-diamine-1,1-dioxide

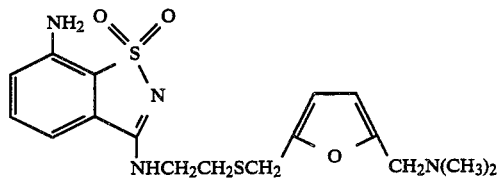

'H-NMR: CDCl₃; δ=2.26 (s, 6H), δ=2.85 (t, 2H), δ=3.25–4.0 (m, b 6H including 3.45, s and 3.75, s), δ=4.4–4.9 (br s, 2H exchanges with D₂O), δ=6.1–6.3 (2d, 2H), δ=6.75–7.7 (m, 4H, reduces to 3H with D₂O).

EXAMPLE 16

N³-[3-(3-piperid-1-ylmethylphenoxy)propyl]-1,2-benzoisothiazole-3,4-diamine-1,1-dioxide

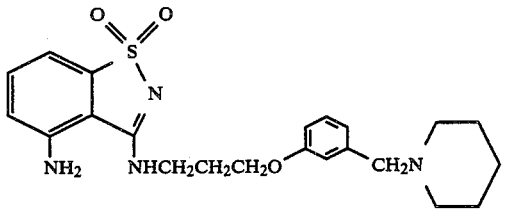

'H-NMR: CDCl₃; δ=1.26–1.8 (m, 6H), δ=1.8–2.2 (m, 2H), δ=2.2–2.55 (m, 4H), δ=3.25–3.6 (m, 4H including 3.45, s), δ=4.06 (t, 2H), δ=4.2–4.7 (br s, 2H exchanges with D₂O), δ=6.65–7.6 (m, 7H), δ=7.35–8.2 (br s, 1H exchanges with D₂O).

EXAMPLE 17

N-[2-(5-dimethylaminomethylfuran-2-ylmethylthio)ethyl]-5,6-dimethoxy-1,2-benzoisothiazole-3-amine-1,1-dioxide

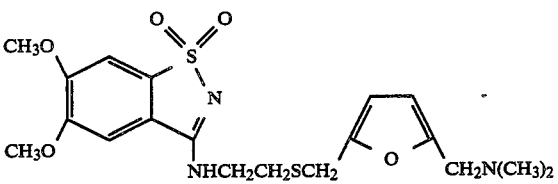

A toluene (50 ml) solution of 5,6-dimethoxy-3-ethoxy-1,2-benzoisothiazole-1,1-dioxide (D5) (0.13 g) was heated under reflux with 2-[(5-dimethylaminomethylfuran-2-yl)methylthio]ethylamine (0.2 g) for 18 h. Evaporation of the solvent and purification of the residue by column chromatography on silica gel using 5% methanolic chloroform as eluant afforded the title compound (0.1 g).

'H-NMR: CDCl₃; δ=2.25 (s, 6H), δ=2.65–3.0 (t, 2H), δ=3.3–4.3 (m, 12H including 3.43, s, 3.71, s and 3.96, s), δ=6.0–6.25 (2d, 2H), δ=7.27 (s, 1H), δ=7.43 (s, 1H), δ=7.75–8.2 (br s, 1H).

Mass spectrum: C₁₉H₂₅N₃O₅S₂—Required: 439.1236, Observed: 439.1235.

EXAMPLE 17b

N³-[2-(5-dimethylaminomethylfuran-2-ylmethylthio)ethyl]-1,2-benzoisothiazole-3,4-diamine-1,1-dioxide

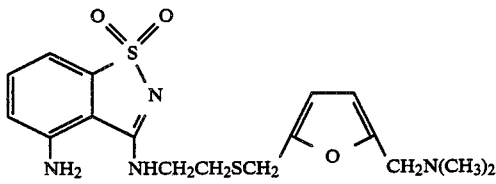

Following the procedures outlined in Example 17, but using methanol as the solvent and heating under reflux for 24 h, 4-amino-3-ethoxy-1,2-benzoisothiazole-1,1-dioxide (D3a) was converted into the title compound mp. 88°–91° (Ethanol/water). 112°–4° (Ethyl acetate/petrol).

EXAMPLE 18

N³-[2-(5-dimethylaminomethylfuran-2-ylmethylthio)ethyl]-6-acetamido-1,2-benzoisothiazole-3-amine-1,1-dioxide

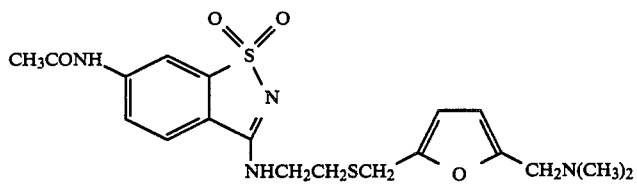

Following the procedures outlined in Example 17, but now using 2-methoxyethanol as solvent and heating under reflux for 3 h, 6-acetamido-3-ethoxy-1,2-benzoisothiazole-1,1-dioxide (D.4) (0.2 g) was converted into the title compound (0.19 g)

mp. 151°-3°.

'H-NMR: CDCl$_3$+CD$_3$OD; $\delta=2.0$ (s, 3H), $\delta=2.28$ (s, 6H), $\delta=2.81$ (t, 2H), $\delta=3.45$ (s, 2H), $\delta=3.60$ (t, 2H), $\delta=3.75$ (s, 2H), $\delta=6.1$-6.25 (2d, 2H), $\delta=7.7$-7.9 (m, 2H), $\delta=8.20$ (d,d, 1H).

Mass spectrum: C$_{19}$H$_{24}$N$_4$O$_4$S$_2$—Required: 436.1243, Observed: 436.1239.

EXAMPLE 19

N³-[3-(3-piperid-1-ylmethylphenoxy)propyl]-1,2-benzoisothiazole-3,6-diamine-1,1-dioxide

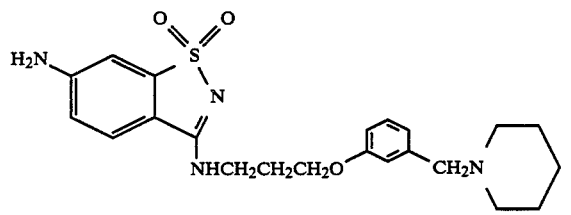

Following the procedures outlined in Example 18 but heating under reflux for 18 h, 6-amino-3-ethoxy-1,2-benzoisothiazole-1,1-dioxide (D3b) (1.0 g) was converted into the title compound (1.2 g)

mp. 185°-7°.

'H-NMR: CDCl$_3$+CD$_3$OD; $\delta=1.3$-1.8 (m, 6H), $\delta=2.16$ (quin. 2H), $\delta=2.3$-2.6 (m, 4H), $\delta=3.51$ (s, 2H), $\delta=3.70$ (t, 2H), $\delta=4.09$ (t, 2H), $\delta=6.6$-7.6 (m, 8H), Mass spectrum: C$_{22}$H$_{28}$N$_4$O$_3$S—Required: 428.1882, Observed: 428.1886.

EXAMPLE 20

N³-[2-(2-guanidinothiazole-4-ylmethylthio)ethyl]-1,2-benzoisothiazole-3,4-diamine-1,1-dioxide

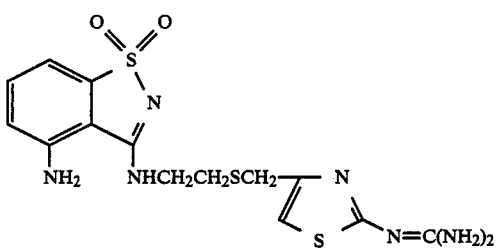

Following the procedure outlined in Example 17, but using methanol as solvent and heating under reflux for 60 h, 4-amino-3-ethoxy-1,2-benzoisothiazole-1,1-dioxide (D3a) (0.5 g) was converted into the title compound (0.06 g).

mp. 200°-2° (dec).

'H-NMR: d$^6$-DMSO; $\delta=2.76$ (t, 2H), $\delta=3.5$-3.8 (m, 4H including 3.65, s), $\delta=6.15$-6.43 (br s, 2H; exchanges with D$_2$O), $\delta=6.56$ (s, 1H), $\delta=6.65$-6.90 (br s, 4H; exchanges with D$_2$O), $\delta=6.9$-7.2 (m, 2H), $\delta=7.32$-7.6 (m, 1H), $\delta=7.7$-8.6 (br s, 1H, exchanges with D$_2$O).

EXAMPLE 21

N-[2-(5-dimethylaminomethylfuran-2-ylmethylthio)ethyl]-4-methyl-1,2-benzoisothiazole-3-amine-1,1-dioxide

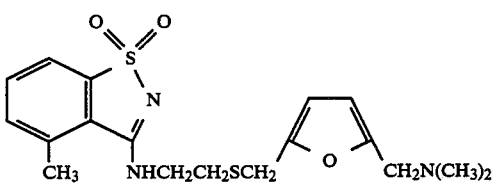

Following the procedures outlined in Example 18, 3-ethoxy-4-methyl-1,2-benzoisothiazole-1,1-dioxide (D2d) was converted into the title compound. mp 90°-92°.

'H-NMR: CDCl$_3$; $\delta=2.18$ (s, 6H), $\delta=2.72$ (s, 3H), $\delta=2.85$ (t, 2H), $\delta=3.35$ (s, 2H), $\delta=3.55$-3.83 (m, 4H, including s, 3.75), $\delta=6.05$-6.2 (2d, 2H), $\delta=6.6$-7 (br s, 1H), $\delta=7.3$-7.85 (m, 3H).

Following the procedures outlined in Example 18, the following Examples were prepared:

EXAMPLE 21b

N-[3-(3-Piperid-1-ylmethylphenoxy)propyl]-6-dimethylsulphamoyl-1,2-benzoisothiazole-3-amine-1,1-dioxide

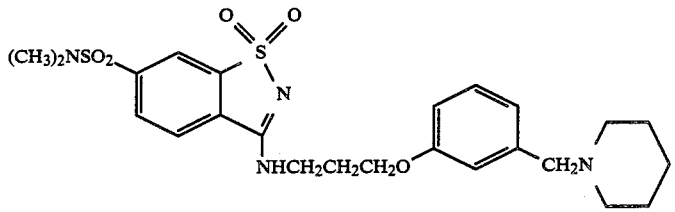

$^1$H NMR: CDCl$_3$+D$_2$O; δ=1.25–1.8 (m, 6H), δ=2.0–2.65 (m, 6H), δ=2.8 (s, 6H), δ=3.50 (s, 2H), δ=3.83 (t, 2H), δ=4.16 (t, 2H), δ=6.60–7.4 (m, 4H), δ=8.05 (m, 2H), δ=8.24 (m, 1H).

EXAMPLE 21c

N-[2-(2-Guanidinothiazole-4-ylmethylthio)ethyl]-6-dimethylsulphamoyl-1,2-benzoisothiazole-3-amine-1,1-dioxide

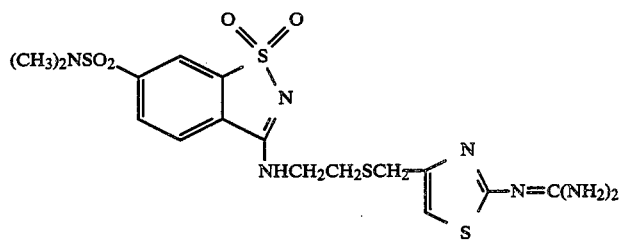

$^1$H NMR: d$^6$ DMSO; δ=2.7 (s, 6H), δ=2.8 (t, 2H), δ=3.16 (s, 2H), δ=3.7 (m), δ=6.56 (s, 1H), δ=6.6–7.2 (brs, 4H exchanges with D$_2$O), δ=8.1–8.65 (m, 3H), δ=9.6–10.1 (brs, 1H exchanges with D$_2$O).

Mass spectrum: C$_{16}$H$_{21}$N$_7$O$_4$S$_4$—Required: 503.0539, Observed: 503.0544.

EXAMPLE 21d

N-[2-(5-Dimethylaminomethylfuran-2-ylmethylthio)ethyl]-6-methylsulphamoyl-1,2-benzoisothiazole-3-amine-1,1-dioxide

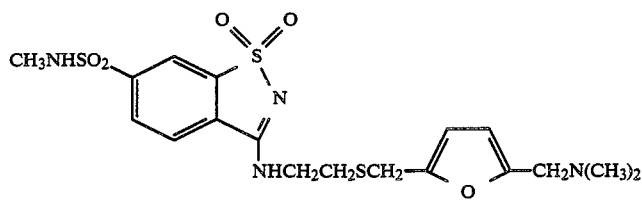

mp. 200°–202° C. (dec).

$^1$H NMR: CDCl$_3$+CD$_3$OD; δ=2.29 (s, 6H), δ=2.65 (s, 3H), δ=2.85 (t, 2H), δ=4.50 (s, 2H), δ=3.70 (t, 2H) δ=3.80 (s, 2H), δ=6.22 (2d, 2H), δ=8.17 (m, 2H), δ=8.33 (m, 1H).

EXAMPLE 21e

N-[3-(3-Piperid-1-ylmethylphenoxy)propyl]-6-methanesulphonylamino-1,2-benzoisothiazole-3-amine-1,1-dioxide

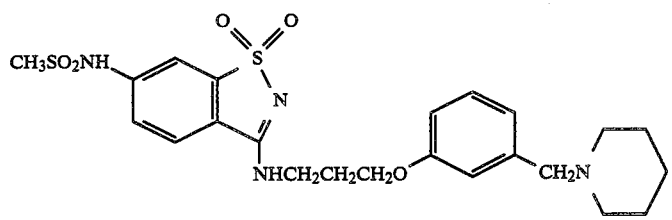

$^1$H-NMR: CDCl$_3$+d$^6$DMSO; δ=1.25–1.75 (m, 6H), δ=2.0–2.6 (m, 6H), δ=3.05 (s, 3H), δ=3.50 (s, 2H), δ=3.72 (brq, 2H), δ=4.08 (t, 2H), δ=6.6–7.35 (m, 4H), δ=7.54 (d, d, 1H), δ=7.70 (d, 1H), δ=8.07 (d, 1H), δ=9.12 (brt, 1H).

Mass spectrum: C$_{23}$H$_{30}$N$_4$O$_5$S$_2$—Required: 506.16575, Observed: 506.16560.

EXAMPLE 21F

N-[2-(2-Guanidinothiazole-4-ylmethylthio)ethyl]-6-acetamido-1,2-benzoisothiazole-3-amine-1,1-dioxide

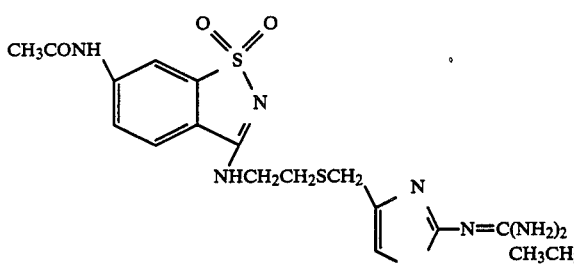

$^1$H NMR: d$^6$DMSO; δ=2.15 (s, 3H), δ=2.79 (t, 2H), δ=3.3–3.75 (m, 2H), δ=3.70 (s, 2H), δ=6.6 (s, 1H), δ=6.95 (brs, 4H), δ=7.75–8.30 (m, 3H), δ=9.50 (brt, 1H), δ=10.65 (brs, 1H).

EXAMPLE 21g

N-[3-(3-Piperid-1-ylmethylphenoxy)propyl]-6-iodo-1,2-benzoisothiazole-3-amine-1,1-dioxide

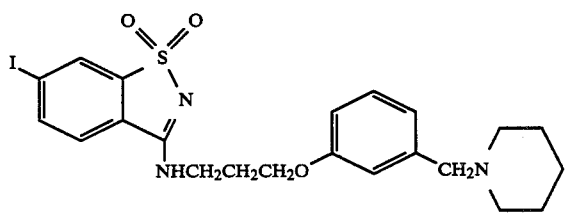

mp. 169°–7° C.
$^1$H NMR: CDCl$_3$; δ=1.55 (m, 6H), δ=2.20 (t, 2H), δ=2.30–2.70 (m, 4H), δ=3.50 (s, 2H), δ=3.80 (t, 2H), δ=4.15 (t, 2H), δ=6.7–7.7 (m, 6H), δ=8.03 (d, d, 1H), δ=8.24 (d, 1H).
Mass spectrum: C$_{22}$H$_{26}$N$_3$O$_3$SI—Required: 534.0742, Observed: 539.0744.

EXAMPLE 21h

N-[2-(2-Guanidinothiazole-4-ylmethylthio)ethyl]-1,2-benzoisothiazole-3,6-diamine-1,1-dioxide

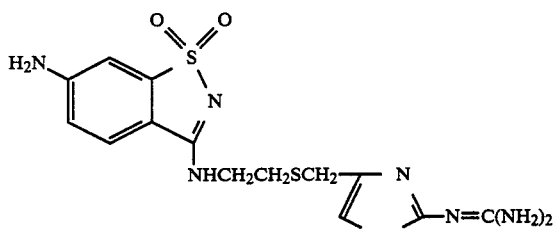

mp. 217°–222° C. (dec).
$^1$H NMR: d$^6$DMSO; δ=2.72 (t, 2H), δ=3.50 (s, 2H), δ=3.65 (t, 2H including s, 1½H ½ mole MeOH), δ=6.40 (s, 2H), δ=6.55 (s, 1H), δ=6.6–7.0 (m, 6H), δ=7.74 (d, 1H), δ=8.85–9.20 (brt, 1H).
Mass spectrum: C$_{14}$H$_{17}$N$_7$O$_2$S$_3$—Required: 411.0607, Observed: 411.0613.

EXAMPLE 21i

N-[3-(3-Piperid-1-ylmethylphenoxy)propyl]-6-propionamido-1,2-benzoisothiazole-3-amine-1,1-dioxide

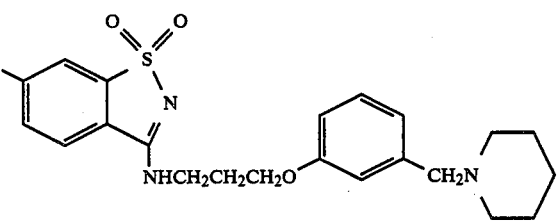

mp. 128°–30° C.
$^1$H NMR: CDCl$_3$+CD$_3$OD; δ=1.22 (t, 3H), δ=1.4–1.67 (m, 6H), δ=2.23 (quin. 2H), δ=2.35–2.52 (m, 6H), δ=3.47 (s, 2H), δ=3.75 (t, 2H), δ=4.10 (t, 2H), δ=6.8–7.4 (m, 3H), δ=7.22 (t, 1H), δ=7.87 (d, 1H), δ=8.02 (d, d, 1H), δ=8.10 (d, 1H).
Mass spectrum: C$_{25}$H$_{32}$N$_4$O$_4$S—Required: 484.2144, Observed: 484.2134.

EXAMPLE 21j

N-[3-(3-Piperid-1-ylmethylphenoxy)propyl]-6-formamido-1,2-benzoisothiazole-3-amine-1,1-dioxide

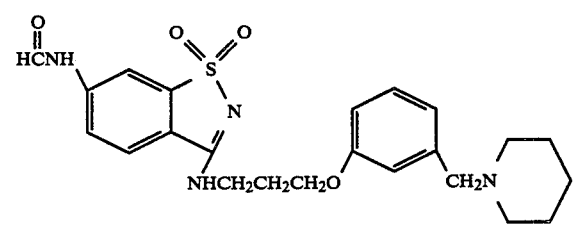

$^1$H NMR: CDCl$_3$; δ=1.0–1.85 (m, 6H), δ=1.85–2.75 (m, 6H), δ=3.2–4.3 (m, 6H including 3.45, s, 2H), δ=6.50–8.50 (m, 8H).
Mass spectrum: C$_{23}$H$_{28}$N$_4$O$_4$S—Required: 456.1831, Observed: 456.1822.

EXAMPLE 22

N$^3$-[2-(5-dimethylaminomethylfuran-2-ylmethylthio)ethyl]-5-amino-1,2-benzoisothiazole-3-amine-1,1-dioxide

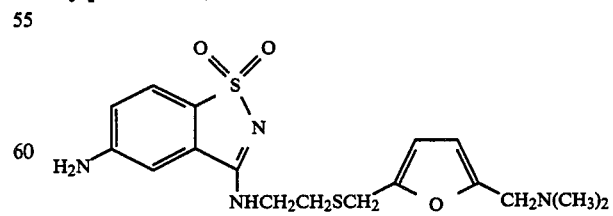

Following the procedures outlined in Example 18, 5-amino-3-ethoxy-1,2-benzoisothiazole-1,1-dioxide (D3c) (0.45 g) was converted to the title compound (0.11 g)
mp. 200°–2°.

¹H-NMR: CDCl₃; δ=2.25 (s, 6H), δ=2.75-3.0 (br t, 2H), δ=3.3-3.8 (m, 8H including 3.44, s, 2H; 3.50, s, 2H, exchangeable with D₂O and 3.75, s, 2H), δ=6.05-6.25 (2d, 2H), δ=7.75-8.6 (m, 4H, 1H exchangeable with D₂O).

EXAMPLE 23

N³-[4-(3-piperid-1-ylmethylphenoxy)butyl]-1,2-benzoisothiazole-3,4-diamine-1,1-dioxide

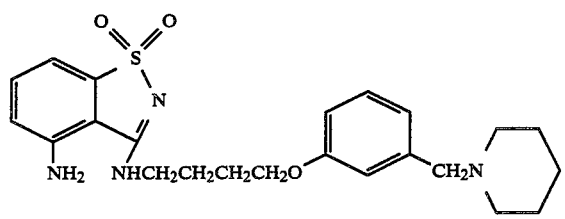

Following the procedures outlined in Example 17, but using methanol as solvent at room temperature for 16 h, 4-amino-3-ethoxy-1,2-benzoisothiazole-1,1-dioxide (D3a) (0.3 g) was converted into the title compound (0.42 g).

mp. 135°-135.5°.

¹H-NMR: CDCl₃; δ=1.25-2.0 (m, 10H), δ=2.3-2.65 (m, 4H), δ=3.0-3.35 (br t, 2H), δ=3.52 (s, 2H), δ=3.8-4.1 (br t, 2H), δ=4.25-4.85 (br s, 2H; exchanges with D₂O), δ=6.65-7.75 (m, 8H; 1H exchanges with D₂O).

Mass spectrum: C₂₃H₃₀N₄O₃S; Required: 442.2039, Observed: 442.2045.

EXAMPLE 24

N³-[3-(3-piperid-1-ylmethylphenoxy)propyl]-6-acetamido-1,2-benzoisothiazole-3-amine-1,1-dioxide

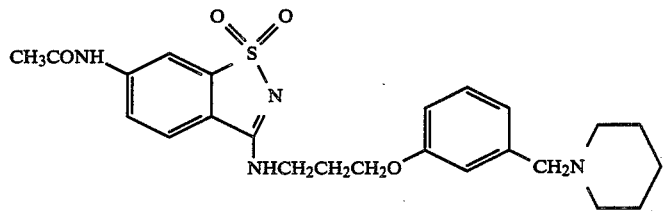

Following the procedures outlined in Example 18, 6-acetamido-3-ethoxy-1,2-benzoisothiazole-1,1-dioxide (D4a) (0.18 g) was converted into the title compound (0.15 g).

mp. 193°-5°.

¹H-NMR: CDCl₃+d₆ DMSO; δ=1.2-1.8 (m, 6H), δ=1.9-2.6 (m, 9H including 2.16, s, 3H), δ=3.44 (s, 2H), δ=3.3-3.85 (m, 2H), δ=3.9-4.2 (t, 2H), δ=6.6-7.3 (m, 4H), δ=7.7-8.3 (m, 3H), δ=8.9-9.2 (brt, 1H exchangeable with D₂O), δ=10.2-10.5 (brs, 1H exchangeable with D₂O).

EXAMPLE 25

N³-[2-(5-Dimethylaminomethylfuran-2-ylmethylthio)ethyl]-6-methylcarbamoylamino-1,2-benzoisothiazole-3-amine-1,1-dioxide

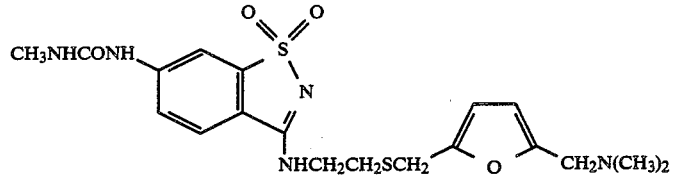

Following the procedures outlined in Example 18, 6-methylcarbamoylamino-3-ethoxy-1,2-benzoisothiazole-1,1-dioxide (D4b) (0.23 g) was converted to the title compound (0.1 g)

¹H-NMR: CDCl₃+CD₃OD; δ=2.29 (s, 6H), δ=2.7-2.95 (m, 5H including 2.83, s, 3H), δ=3.45-3.75 (m, 6H including 3.50, s, 2H and 3.78, s, 2H), δ=6.1-6.25 (2d, 2H), δ=7.6-8.05 (m, 3H).

EXAMPLE 26

N³-[2-(5-Dimethylaminomethylfuran-2-ylmethylthio)ethyl]-4-acetamido-1,2-benzoisothiazole-3-amine-1,1-dioxide

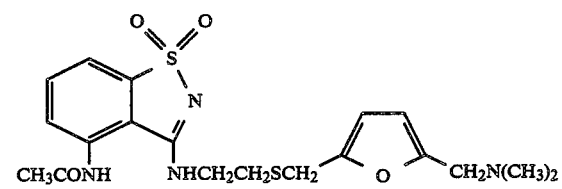

Following the procedures outlined in Description 4, N³-[2-(5-dimethylaminomethylfuran-2-ylmethylthio)ethyl]-1,2-benzoisothiazole-3,4-diamine-1,1-dioxide (0.27 g) was converted to the title compound (0.22 g)

¹H-NMR: CDCl₃+D₂O; δ=2.08 (s, 6H), δ=2.36 (s, 3H), δ=2.82 (t, 2H), δ=3.3-3.66 (m, 4H including 3.41, s, 2H), δ=3.78 (s, 2H), δ=6.18 (s, 2H), δ=7.55-7.9 (m, 3H),

EXAMPLE 27

N³-[3-(3-Piperid-1-ylmethylphenoxy)propyl]-1,2-benzoisothiazole-3-amine-1-oxide

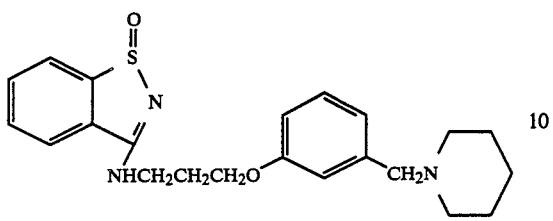

A solution of N-[3-(3-Piperid-1-ylmethylphenoxy)-propyl]-1,2-benzoisothiazole-3-amine (D4) (0.2 g) in methanol (20 ml) and 5N hydrochloric acid (5 ml) was stirred at room temperature with m-chloroperbenzoic acid (0.1 g) for 30 min. Concentration, basification with potassium carbonate and extraction with dichloromethane afforded, on evaporation to dryness, the title compound (0.15 g).

¹H-NMR: CDCl₃; δ=1.2–1.8 (m, 6H), δ=1.95–2.6 (m, 6H), δ=3.43 (s, 2H), δ=3.6–3.9 (br d,t 2H), δ=4.09 (t, 2H), δ=6.7–8.1 (m, 9H, 1H exchanges with D₂O).

EXAMPLE 28

N-[3-(3-{1-Piperidylmethyl}phenoxy)propyl]-6-N-methylsulphamoyl-1,2-benzoisothiazole-3-amine-1,1-dioxide

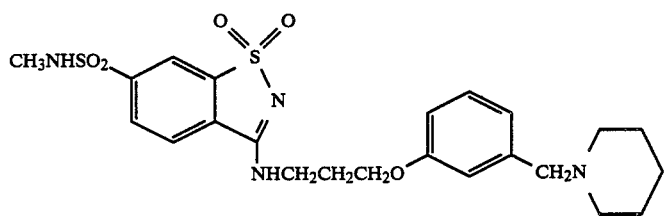

A solution of 3-methylthio-6-N-methylsulphamoyl-1,2-benzoisothiazole-1,1-dioxide (0.53 g) and 3-(3-{piperidylmethyl}phenoxy)propylamine (0.43 g) in dimethoxyethane (15 ml) and methanol (10 ml) was stirred at room temperature for 24 hrs. On evaporation, the residue was purified by column chromatography (silica, 5% MeOH/CHCl₃) to give the title compound as a foam (0.5 g).

NMR (CDCl₃): δ=8.4–7.9 (m., 3H), 7.85–6.65 (m., 4H), 6.5–5.0 (br s., 2H exchanges with D₂O), 4.09 (t, 2H), 3.75 (t, 2H), 3.57 (s, 2H), 2.85–2.0 (br m., 9H), 2.0–1.2 (br m., 6H).

Mass Spectrum: C₂₃H₃₀N₄O₅S₂—Required: 506.1658, Observed: 506.1670.

FOLLOWING THE PROCEDURE OUTLINED IN EXAMPLE 28, THE FOLLOWING COMPOUNDS WERE PREPARED

EXAMPLE 29

N-[2-(5-Dimethylaminomethylfuran-2-ylmethylthio)ethyl]-6-sulphamoyl-1,2-benzoisothiazole-3-amine-1,1-dioxide

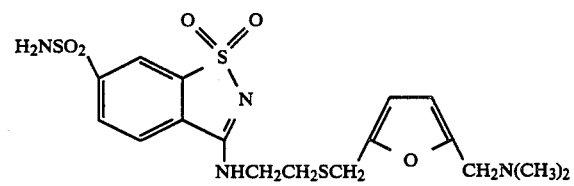

EXAMPLE 30

N-[3-(3-{1-Piperidylmethyl}phenoxy)propyl]-6-sulphamoyl-1,2,-benzoisothiazole-3-amine-1,1-dioxide

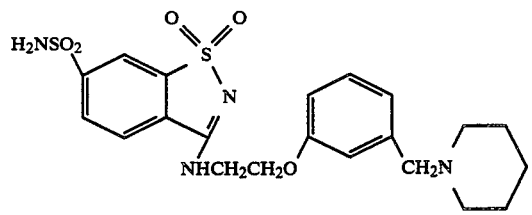

EXAMPLE 31

N-[2-(2-Guanidinothiazole-4-ylmethylthio)ethyl]-6-sulphamoyl-1,2-benzoisothiazole-3-amine-1,1-dioxide

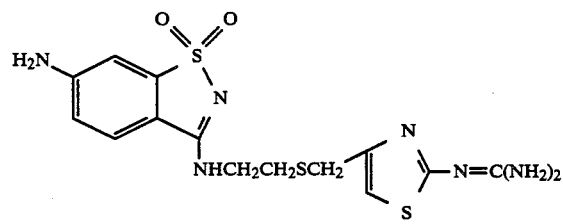

EXAMPLE 32

N$^3$-[2-(5-Dimethylaminomethylfuran-2-ylmethylthio)ethyl]-1,2-benzoisothiazole-3,4-diamine-1,1-dioxide

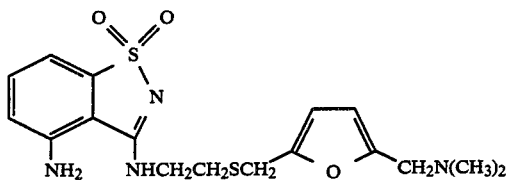

To a stirred solution of N$^3$-[2-mercapto ethyl]-1,2-benzoisothiazole-3,4-diamine-1,1-dioxide (D.9, 0.11 g) in concentrated hydrochloric acid (0.4 ml) under nitrogen at −10° C. was added 5-dimethylaminomethyl-2-furanmethanol (0.08 g). After stirring at room temperature overnight, the reaction mixture was worked-up as described in Example 2 to afford the title compound.

Pharmacological Data Section

The ability of the compounds of the invention to modify the pH of gastric acid secretion was investigated as follows:

The perfused rat stomach preparation

The modified (1) perfused stomach preparation (2) of the urethane (25% solution) anaesthetised rat, maintained at 37° C., allows the continuous measurement of pH during basal and stimulated acid secretion.

The lumen of the stomach of male Wistar rats (approximately 200 g bodyweight) was perfused, via a cannula designed to reduce the dead space of the stomach, with 5% glucose solution (37° C.) at the rate of 3 ml/min. The perfusate was forced over the surface of the secretory mucosa only, the antrum being excluded. The effluent then passed over a microflow-type glass pH electrode via a collecting funnel situated in the nonglandular forestomach.

The secretagogue histamine was administered as a constant intravenous infusion to produce a steady rate of acid secretion. Test compounds were administered in solution as bolus intravenous injections and any effect on the pH of the perfusate noted. The perfusate pH was recorded on a potentiometric recorder and anti-secretory responses were measured in terms of the maximal reduction in hydrogen-ion concentration expressed as a percentage of the control concentration.

See Table I.

References (1) Ghosh, M. N. and Schild, H. O. (1958). Br. J. Pharmacol., 13, 54–61.

(2) Parsons, M. E. (1970). Ph.D. Thesis, University of London.

TABLE I

| Compound of Example No. | Dose (μmole/kg) | Inhibition |
|---|---|---|
| 1 | 0.2 | 87% |
| 2 | 0.2 | 100% |
| 3 | 1 | 100% |
| 5 | 2 | 80% |
| 6 | 1 | 75% |
| 7 | 0.5 | 68% |
| 8 | 5 | 75% |
| 9 | 0.1 | 89% |
| 10 | 0.5 | 100% |
| 11 | 0.5 | 100% |

TABLE I-continued

| Compound of Example No. | Dose (μmole/kg) | Inhibition |
|---|---|---|
| 12 | 0.5 | 94% |
| 14 | 0.2 | 60% |
| 15 | 0.4 | 60% |
| 16 | 0.1 | 100% |
| 20 | 0.2 | 100% |

Guinea-pig isolated atria

This test is designed to specifically detect histamine H$_2$-receptor antagonists. Guinea-pigs of either sex, weighing between 250 and 500 g, were killed by cervical dislocation and exsanguination. The heart was removed and placed in cold McEwens solution. The atria were dissected free and mounted in a jacketed 5 ml capacity tissue bath containing McEwens solution maintained at 32° C. and gassed with a 95% oxygen, 5% carbon dioxide gas mixture. Atrial beating was detected by an auxotonic lever and from thence recorded on a Devices MX2 hot wire pen recorder. Atrial rate was derived from the amplified force signal using a Devices Instantaneous Ratemeter and recorded on the MX2 pen recorder. The addition of histamine to the tissue bath resulted in increases in both the rate and force of atrial beating. To avoid disruption of the tissue by repeated washing, responses to cumulative concentrations of histamine were obtained in the absence (control) and then presence of various concentrations of test compounds. The ability to antagonise histamine mediated positive chronotropic responses of this tissue is believed to be specific for H$_2$-receptor antagonists. Such activity was assessed by examining the ability of test compounds to shift to the right the plotted concentration/response curves to histamine. A less than 5-fold decrease in histamine potency was taken as inactive, 5–10 fold as slightly active and 10 fold or greater as active.

See Table II.

TABLE II

| Compound of Example No. | Concentration Molar | Activity (Decrease in Histamine Potency) |
|---|---|---|
| 1 | $7.5 \times 10^{-7}$ | Active |
| 2 | $7.5 \times 10^{-8}$ | Active |
| 3 | $5 \times 10^{-7}$ | Active |
| 6 | $5 \times 10^{-7}$ | Active |
| 8 | $1 \times 10^{-5}$ | Active |
| 10 | $2.5 \times 10^{-7}$ | Active |
| 11 | $1 \times 10^{-7}$ | Active |
| 12 | $1 \times 10^{-6}$ | Active |
| 13 | $1 \times 10^{-6}$ | Active |
| 14 | $5 \times 10^{-7}$ | Active |
| 16 | $7.5 \times 10^{-8}$ | Active |
| 20 | $2.5 \times 10^{-7}$ | Active |

Toxicity

No drug-induced toxic effects were observed in these tests.

We claim:

1. A compound of formula (I) or a pharmaceutically acceptable salt, a compound of formula (I) quaternized by an optionally substituted alkyl halide selected from the group consisting of C$_{1-4}$ alkyl, C$_{3-6}$ cycloalkyl, C$_{3-6}$ cycloalkyl C$_{1-4}$ alkyl or phenyl C$_{1-4}$ alkyl halide, N-oxide of the NH-Het moiety of formula (I) or hydrate thereof:

R₁—Ar—(CH₂)ₐ—X—(CH₂)ᵦ—NH—Het    (I)

wherein:

$R_1$ is hydrogen, halogen, hydroxy, $C_{1-4}$ alkyl, $C_{1-4}$ alkoxy, or amino or guanidino, the or any amino moiety being optionally substituted by one or two $C_{1-4}$ alkyl optionally substituted by halogen, or an aminomethylene group of formula (a),

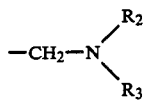   (a)

in which $R_2$ and $R_3$ are the same or different and are hydrogen, $C_{1-4}$ alkyl, $C_{3-6}$ cycloalkyl, $C_{3-6}$ cycloalkyl $C_{1-4}$ alkyl or phenyl $C_{1-4}$ alkyl, or $R_2$ and $R_3$ together with the nitrogen atom to which they are attached are morpholino, pyrrolidino or piperidino;

Ar is furandiyl, thiophendiyl, phenylene, thiazolediyl or thiadiazolediyl;

a is 0 or an integer 1 or 2;

X is —S—, —O—, —CH₂—,

or —NH—;

b is an integer from 2 to 5; and

Het is bicyclic heteroaryl group of formula,

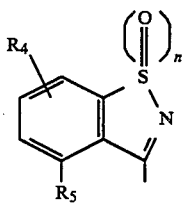

in which $R_4$ is hydrogen and $R_5$ is hydrogen, halogen, $C_{1-6}$ alkyl, trifluoromethyl, nitro, cyano, hydroxy, $C_{1-6}$ alkoxy, $C_{1-6}$ alkylthio, carboxy, amino, aminocarbonyl, aminocarbonylamino, amino-thiocarbonylamino, aminosulphonyl, $C_{1-6}$ alkylsulphonyl, $C_{1-6}$ alkylsulphinyl, $C_{1-6}$ alkylsulphonylamino, $C_{1-6}$ alkylsulphinylamino, phenylsulphonyl, phenylsulphinyl or a group of formula (d) or (e), R₆—CY—    (d)

R₆—CY—Z—    (e)

in which $R_6$ is hydrogen, $C_{1-6}$ alkyl, $C_{1-6}$ alkoxy, $C_{1-6}$ alkylthio, phenyl, phenoxy or phenylthio, Y is oxygen or sulphur and Z is oxygen, sulphur or N—R₇, R₇ being hydrogen or $C_{1-6}$ alkyl, the $C_{1-6}$ alkyl group or the $C_{1-6}$ alkyl moiety of any of the foregoing $C_{1-6}$ alkyl-containing groups for $R_5$ being optionally substituted by phenyl, the amino group or the amino moiety of any of the foregoing amino-containing groups for $R_5$ being optionally substituted by one or two $C_{1-6}$ alkyl, phenyl or phenyl-$C_{1-4}$ alkyl or optionally N-disubstituted by $C_{4-5}$ polymethylene, and the phenyl moiety of any of the foregoing phenyl-containing groups for $R_5$ being optionally substituted by $C_{1-6}$ alkyl, $C_{1-6}$ alkoxy, halogen, nitro or trifluoromethyl, and n is 0 or an integer 1 or 2.

2. A compound according to claim 1, wherein Ar is 2,5-furandiyl; 2,5-thiophendiyl; 1,3-phenylene; or 2,4-thiazolediyl.

3. A compound according to claim 1, wherein Ar is furandiyl, thiophendiyl or phenylene and $R_1$ is an aminomethylene group of formula (a), as defined in claim 1.

4. A compound according to claim 1, wherein Ar is thiazolediyl and $R_1$ is guanidino, any amino moiety being optionally substituted by one or two $C_{1-4}$ alkyl.

5. A compound according to claim 1, wherein a is 0 or the interger 1.

6. A compound according to claim 1, wherein X is —S—, —O— or —CH₂—.

7. A compound according to claim 1, wherein b is an integer 2, 3 or 4.

8. A compound according to claim 1, wherein $R_5$ is hydrogen, trifluoromethyl, nitro, cyano, hydroxy, $C_{1-6}$ alkoxy, $C_{1-6}$ alkylthio, or amino optionally substituted by one or two $C_{1-6}$ alkyl or phenyl $C_{1-4}$ alkyl or optionally N-disubstituted by $C_{4-5}$ polymethylene, or $C_{1-6}$ alkylsulphonyl or phenylsulphonyl, the phenyl moiety being optionally substituted by $C_{1-6}$ alkyl, $C_{1-6}$ alkoxy, halogen, nitro or trifluoromethyl, or a group of formula (d) in which Y is oxygen and $R_6$ is as defined in claim 1, or a group of formula (e) in which Y is oxygen, Z is N-R₇ and $R_6$ and $R_7$ are as defined in claim 1.

9. A compound according to claim 1, wherein $R_5$ is hydrogen, halogen, $C_{1-6}$ alkyl, trifluoromethyl, nitro, cyano, $C_{1-6}$ alkoxy, or amino, aminocarbonylamino or aminosulphonyl, the amino moiety being optionally substituted by one or two $C_{1-6}$ alkyl, phenyl or phenyl-$C_{1-4}$ alkyl or optionally N-disubstituted by $C_{4-5}$ polymethylene, or $C_{1-6}$ alkylsulphonylamino or a group of formula (e) in which $R_6$ is hydrogen or $C_{1-6}$ alkyl, Y is oxygen and Z is NH.

10. A compound according to claim 9, wherein $R_5$ is selected from the group consisting of hydrogen, chloro, bromo, iodo, methyl, trifluoromethyl, nitro, cyano, methoxy, amino, methylaminocarbonylamino, aminosulphonyl, methylaminosulphonyl, dimethylaminosulphonyl, methylsulphonylamino, foramido, acetamido and propionamido.

11. A compound according to claim 10, wherein $R_5$ is is selected from the group consisting of hydrogen, nitro, amino, methylaminosulphonyl, dimethylaminosulphonyl, acetamido and propionamido.

12. A compound according to claim 3, wherein a is 0 or an integer 1, X is —S—, —O— or —CH₂—, b is an integer from 2 to 5 and $R_5$ is hydrogen, trifluoromethyl, nitro, cyano, hydroxy, $C_{1-6}$ alkoxy, $C_{1-6}$ alkylthio, or amino optionally substituted by one or two $C_{1-6}$ alkyl or phenyl $C_{1-4}$ alkyl or optionally N-disubstituted by $C_{4-5}$ polymethylene, or $C_{1-6}$ alkylsulphonyl or phenylsulphonyl, the phenyl moiety being optionally substituted by $C_{1-6}$ alkyl, $C_{1-6}$ alkoxy, halogen, nitro or trifluoromethyl, or a group of formula (d) in which Y is oxygen and $R_6$ is as defined in claim 1, or a group of formula (e) in which Y is oxygen, Z is N-R₇ and $R_6$ and $R_7$ are as defined in claim 1, and n is 2.

13. A compound according to claim 1, wherein n is 1 or 2.

14. A compound which is selected from the group consisting of:

N-[2-(5-dimethylaminomethylfuran-2-ylmethylthio)e-
thyl]-4-nitro-1,2-benzoisothiazole-3-amine-1,1-diox-
ide;

N-[3-(3-dimethylaminomethylphenoxy)propyl]-4-nitro-
1,2-benzoisothiazole-3-amine-1,1-dioxide;

N-[3-(4-dimethylaminomethylphenoxy)propyl]-4-nitro-
1,2-benzoisothiazole-3-amine-1,1-dioxide;

N-[3-(3-piperid-1-ylmethylphenoxy)propyl]-4-nitro-1,2-
benzoisothiazole-3-amine-1,1-dioxide;

N-[2-(5-dimethylaminomethylthiophen-2-ylmethylthi-
o)ethyl]-4-nitro-1,2-benzoisothiazole-3-amine-1,1-
dioxide;

N-[2-(3-dimethylaminomethylphenoxy)ethyl]-4-chloro-
1,2-benziosothiazole-3-amine-1,1-dioxide;

$N^3$-[3-(3dimethylaminomethylphenoxy)propyl]-1,2-
benzoisothiazole-3,4-diamine-1,1-dioxide;

$N^3$-[3-(4-dimethylaminomethylphenoxy)propyl]-1,2-
benzoisothiazole-3,4-diamine-1,1-dioxide;

$N^3$-[3-(3-piperid-1-ylmethylphenoxy)propyl]-1,2-ben-
zoisothiazole-3,4-diamine-1,1-dioxide;

$N^3$-[2-(5-dimethylaminomethylthiophen-2-ylmethylthi-
o)ethyl]-1,2-benzoisothiazole-3,4-diamine-1,1-diox-
ide; or a pharmaceutically acceptable salt of a compound se-
lected from said group of compounds, or a compound
selected from said group of compounds quaternized by
an optionally substituted alkyl halide selected from the
group consisting of $C_{1-4}$ alkyl, $C_{3-6}$ cycloalkyl, $C_{3-6}$
cycloalkyl $C_{1-4}$ alkyl or phenyl $C_{1-4}$ alkyl halide, or an
N-oxide of the NH-Het moiety of a compound selected
from said group of compounds or a hydrate of a com-
pound selected from said group of compounds.

15. A compound which is selected from the group
consisting of:

N-[2-(5-dimethylaminomethylfuran-2-ylmethylthio)e-
thyl]-4-chloro-1,2-benzoisothiazole-3-amine-1,1-diox-
ide;

N-[2-(5-dimethylaminomethylfuran-2-ylmethylthio)e-
thyl]-4-iodo-1,2-benzoisothiazole-3-amine-1,1-diox-
ide;

N-[2-(5-dimethylaminomethylfuran-2-ylmethylthio)e-
thyl]-4-cyano-1,2-benzoisothiazole-3-amine-1,1-diox-
ide;

N-[2-(5-dimethylaminomethylfuran-2-ylmethylthio)e-
thyl]-4-methyl-1,2-benzoisothiazole-3-amine-1,1-
dioxide;

$N^3$-[2-(5-dimethylaminomethylfuran-2-ylmethylthio)e-
thyl]-4-acetamido-1,2-benzoisothiazole-3-amine-1,1-
dioxide;

$N^3$-[4-(3-piperid-1-ylmethylphenoxy)butyl]-1,2-ben-
zoisothiazole-3,4-diamine-1,1-dioxide;

N-[2-(2-guanidinothiazol-4-ylmethylthio)ethyl]-4-nitro-
1,2-benzoisothiazole-3-amine-1,1-dioxide;

N-[2-(2-guanidinothiazol-4-ylmethylthio)ethyl]-1,2-
benzoisothiazole-3,4-diamine-1,1-dioxide; or a pharmaceutically acceptable salt of a compound se-
lected from said group of compounds, or a compound
selected from said group of compounds quaternized by
an optionally substituted alkyl halide selected from the
group consisting of $C_{1-4}$ alkyl, $C_{3-6}$ cycloalkyl, $C_{3-6}$
cycloalkyl $C_{1-4}$ alkyl or phenyl $C_{1-4}$ alkyl halide, or an
N-oxide of the NH-Het moiety of a compound selected
from said group of compounds or a hydrate of a com-
pound selected from said group of compounds.

16. A compound which is selected from the group
consisting of:

$N^3$-[2-(5-dimethylaminomethylfuran-2-ylmethylthio)e-
thyl]-1,2-benzoisothiazole-3,4-diamine-1,1-dioxide; or a pharmaceutically acceptable salt thereof, or said com-
pound quaternized by an optionally substituted alkyl
halide selected from the group consisting of $C_{1-4}$ alkyl,
$C_{3-6}$ cycloalkyl, $C_{3-6}$ cycloalkyl $C_{1-4}$ alkyl or phenyl
$C_{1-4}$ alkyl halide, or an N-oxide of the NH-Het moiety
of said compound or a hydrate of said compound.

17. A pharmaceutical composition, which comprises
a pharmaceutically effective amount of a compound of
formula (I), as defined in claim 1, or a pharmaceutically
acceptable salt, a compound of formula (I) quaternized
by an optionally substituted alkyl halide selected from
the group consisting of $C_{1-4}$ alkyl, $C_{3-6}$ cycloalkyl, $C_{3-6}$
cycloalkyl $C_{1-4}$ alkyl or phenyl $C_{1-4}$ alkyl halide, N-
oxide of the NH-Het moiety of formula (I) or hydrate
thereof, and a pharmaceutically acceptable carrier.

18. A method of treating or preventing disorders in
mammals such as humans caused or exacerbated by
excess gastric acid secretion, such as peptic ulcer, com-
prising administering to a mammal a pharmaceutically
effective amount of a compound of formula (I), as de-
fined in claim 1, or a pharmaceutically acceptable salt, a
compound of formula (I) quaternized by an optionally
substituted alkyl halide selected from the group consist-
ing of $C_{1-4}$ alkyl, $C_{3-6}$ cycloalkyl, $C_{3-6}$ cycloalkyl $C_{1-4}$
alkyl or phenyl $C_{1-4}$ alkyl halide, N-oxide of the NH-
Het moiety of formula (I) or hydrate thereof.

* * * * *